(12) United States Patent
Hon

(10) Patent No.: US 10,327,478 B2
(45) Date of Patent: *Jun. 25, 2019

(54) ELECTRONIC CIGARETTE

(71) Applicant: FONTEM HOLDINGS 1 B.V., Amsterdam (NL)

(72) Inventor: Lik Hon, Beijing (CN)

(73) Assignee: FONTEM HOLDINGS 1 B.V., Amsterdam (NL)

( * ) Notice: Subject to any disclaimer, the term of this patent is extended or adjusted under 35 U.S.C. 154(b) by 0 days.

This patent is subject to a terminal disclaimer.

(21) Appl. No.: 15/895,147

(22) Filed: Feb. 13, 2018

(65) Prior Publication Data

US 2018/0168234 A1      Jun. 21, 2018

Related U.S. Application Data

(60) Continuation of application No. 15/632,030, filed on Jun. 23, 2017, now Pat. No. 10,123,569, which is a (Continued)

(30) Foreign Application Priority Data

Apr. 29, 2003  (CN) .................................. 03 1 11582

(51) Int. Cl.
*A61M 15/06* (2006.01)
*A61K 9/00* (2006.01)
(Continued)

(52) U.S. Cl.
CPC .......... *A24F 47/008* (2013.01); *A24B 15/167* (2016.11); *A24F 47/002* (2013.01);
(Continued)

(58) Field of Classification Search
None
See application file for complete search history.

(56) References Cited

U.S. PATENT DOCUMENTS 705,919 A    7/1902 Gill
1,147,416 A   7/1915 MacDonald
(Continued)

FOREIGN PATENT DOCUMENTS

CA    2562581 A1   10/2005
CN    2047485 U    11/1989
(Continued)

OTHER PUBLICATIONS

Australian Patent Office, "Examination Report for Singapore Patent Application No. 200505930-8", dated May 4, 2006, 3 pages.
(Continued)

*Primary Examiner* — Thor S Campbell
(74) *Attorney, Agent, or Firm* — Perkins Coie LLP; Kenneth H. Ohriner

(57) ABSTRACT

An electronic cigarette comprises nicotine without harmful tar. The cigarette includes a shell, a cell, nicotine solution, control circuit, and an electro-thermal vaporization nozzle installed in the air suction end of the shell. The advantages of the present invention are smoking without tar, reducing the risk of cancer, the user still gets a smoking experience, the cigarette is not lit, and there is no fire danger.

27 Claims, 7 Drawing Sheets

Related U.S. Application Data continuation of application No. 15/091,296, filed on Apr. 5, 2016, now Pat. No. 9,713,346, which is a continuation of application No. 14/328,561, filed on Jul. 10, 2014, now Pat. No. 9,364,027, which is a continuation of application No. 13/921,582, filed on Jun. 19, 2013, now Pat. No. 8,910,641, which is a continuation of application No. 13/088,276, filed on Apr. 15, 2011, now Pat. No. 8,511,318, which is a division of application No. 10/547,244, filed as application No. PCT/CN2004/000182 on Mar. 8, 2004, now abandoned.

(51) Int. Cl.

| | | |
|---|---|---|
| H02J 7/00 | (2006.01) | |
| H05B 1/02 | (2006.01) | |
| H05B 3/00 | (2006.01) | |
| A24B 15/16 | (2006.01) | |
| A24F 47/00 | (2006.01) | |

(52) U.S. Cl.
CPC ............ *A61K 9/007* (2013.01); *H02J 7/0045* (2013.01); *H02J 7/0052* (2013.01); *H05B 1/0202* (2013.01); *H05B 1/0244* (2013.01); *H05B 3/0014* (2013.01)

(56) References Cited

U.S. PATENT DOCUMENTS

| | | | |
|---|---|---|---|
| 1,775,947 A | 9/1930 | Robinson | |
| 2,057,353 A | 10/1936 | Whittemore et al. | |
| 2,516,843 A | 8/1950 | Bakst | |
| 2,545,851 A | 3/1951 | Kardos | |
| 2,696,382 A | 12/1954 | Gelardin | |
| 3,200,819 A | 8/1965 | Gilbert | |
| 3,281,637 A | 10/1966 | Hultquist | |
| 3,340,647 A | 9/1967 | Lathrop | |
| 3,479,561 A | 11/1969 | Janning | |
| 3,551,643 A | 12/1970 | Pricenski | |
| 3,719,795 A * | 3/1973 | Bolomier | A61H 33/12 392/404 |
| 3,789,840 A * | 2/1974 | Rosenblatt | A24F 47/002 131/270 |
| 3,832,579 A | 8/1974 | Arndt | |
| 4,207,457 A | 6/1980 | Haglund et al. | |
| 4,228,925 A | 10/1980 | Mendelovich | |
| 4,446,862 A | 5/1984 | Baum et al. | |
| 4,574,181 A | 3/1986 | Spector | |
| 4,692,590 A | 9/1987 | Spector | |
| 4,771,796 A * | 9/1988 | Myer | A24F 47/002 131/273 |
| 4,878,107 A | 10/1989 | Hopper | |
| 4,922,901 A | 5/1990 | Brooks et al. | |
| 4,945,929 A | 8/1990 | Egilmex | |
| 4,945,931 A | 8/1990 | Gori | |
| 4,947,874 A | 8/1990 | Brooks et al. | |
| 4,947,875 A | 8/1990 | Brooks et al. | |
| 5,038,394 A * | 8/1991 | Hasegawa | A01M 1/2077 392/392 |
| 5,060,671 A * | 10/1991 | Counts | A24F 47/008 128/202.21 |
| 5,080,114 A | 1/1992 | Rudolph et al. | |
| 5,095,921 A | 3/1992 | Losee et al. | |
| 5,144,962 A * | 9/1992 | Counts | A24F 47/008 128/200.14 |
| 5,177,424 A | 1/1993 | Connors | |
| 5,190,060 A | 3/1993 | Gerding et al. | |
| 5,235,157 A | 8/1993 | Blackburn | |
| 5,261,424 A | 11/1993 | Sprinkel | |
| 5,261,601 A * | 11/1993 | Ross | A61M 15/0085 128/200.16 |
| 5,269,327 A | 12/1993 | Counts et al. | |
| 5,285,050 A | 2/1994 | Blackburn | |
| 5,388,574 A | 2/1995 | Ingebrethsen | |
| 5,497,791 A | 3/1996 | Bowen | |
| 5,498,855 A | 3/1996 | Deevi | |
| 5,505,214 A | 4/1996 | Collins et al. | |
| 5,530,225 A | 6/1996 | Hajaligol | |
| 5,591,368 A | 1/1997 | Fleischhauer | |
| 5,665,262 A | 9/1997 | Hajaligol | |
| 5,666,977 A | 9/1997 | Higgins et al. | |
| 5,692,291 A | 12/1997 | Deevi | |
| 5,708,258 A | 1/1998 | Counts | |
| 5,743,251 A | 4/1998 | Howell et al. | |
| 5,750,964 A | 5/1998 | Counts | |
| 5,819,756 A | 10/1998 | Mielordt | |
| 5,865,185 A | 2/1999 | Collins | |
| 5,880,439 A | 3/1999 | Deevi | |
| 5,894,841 A * | 4/1999 | Voges | A24F 47/008 128/200.14 |
| 5,902,501 A | 5/1999 | Nunnally | |
| 5,924,784 A | 7/1999 | Chliwnyj et al. | |
| 5,934,289 A * | 8/1999 | Watkins | A24F 47/008 128/202.21 |
| 5,954,979 A | 9/1999 | Counts | |
| 6,016,038 A | 1/2000 | Mueller et al. | |
| 6,040,560 A | 3/2000 | Fleischhauer et al. | |
| 6,116,237 A | 9/2000 | Schultz et al. | |
| 6,155,268 A | 12/2000 | Takeuchi | |
| 6,175,687 B1 * | 1/2001 | Imamura | F24F 6/043 392/395 |
| 6,178,969 B1 * | 1/2001 | St. Charles | A24F 47/002 131/273 |
| 6,196,218 B1 * | 3/2001 | Voges | A24F 47/002 128/200.14 |
| 6,211,626 B1 | 4/2001 | Lys et al. | |
| 6,234,167 B1 * | 5/2001 | Cox | A61M 15/0083 128/200.14 |
| 6,443,146 B1 | 9/2002 | Voges | |
| 6,459,919 B1 | 10/2002 | Lys et al. | |
| 6,491,516 B1 | 12/2002 | Tal et al. | |
| 6,501,052 B2 | 12/2002 | Cox et al. | |
| 6,532,965 B1 | 3/2003 | Abhulimen et al. | |
| 6,557,552 B1 | 5/2003 | Cox et al. | |
| 6,598,602 B1 | 7/2003 | Sjoholm | |
| 6,598,607 B2 | 7/2003 | Adiga | |
| 6,719,443 B2 | 4/2004 | Gutstein et al. | |
| 6,772,756 B2 | 8/2004 | Shayan et al. | |
| 6,794,613 B1 | 9/2004 | Krumholz | |
| 6,854,470 B1 | 2/2005 | Pu | |
| 7,300,178 B2 | 11/2007 | Helou | |
| 7,726,320 B2 | 6/2010 | Robinson | |
| 7,997,280 B2 | 8/2011 | Rosenthal | |
| 8,899,239 B2 * | 12/2014 | Hon | A24F 47/002 131/270 |
| 8,910,641 B2 * | 12/2014 | Hon | A24F 47/002 128/202.21 |
| 9,364,027 B2 * | 6/2016 | Hon | A24F 47/002 |
| 9,456,632 B2 * | 10/2016 | Hon | A24F 47/008 |
| 9,713,346 B2 * | 7/2017 | Hon | A24F 47/002 |
| 2002/0078948 A1 | 6/2002 | Hindle | |
| 2003/0011579 A1 | 1/2003 | Gong | |
| 2003/0189826 A1 | 10/2003 | Yoon | |
| 2003/0209531 A1 | 11/2003 | Mattis | |
| 2003/0213794 A1 | 11/2003 | Krieger | |
| 2003/0226837 A1 | 12/2003 | Blake | |
| 2004/0112893 A1 | 6/2004 | Okuda | |
| 2004/0129696 A1 | 7/2004 | Doi | |
| 2004/0149282 A1 | 8/2004 | Hickle | |
| 2004/0175521 A1 | 9/2004 | Nakamura | |
| 2004/0182403 A1 | 9/2004 | Andersson et al. | |
| 2005/0016550 A1 | 1/2005 | Katase | |
| 2005/0077869 A1 | 4/2005 | Yueh | |
| 2005/0205559 A1 | 9/2005 | Kikuchi | |
| 2006/0047368 A1 | 3/2006 | Maharajh et al. | |
| 2006/0196518 A1 * | 9/2006 | Hon | A24F 47/002 131/360 |
| 2007/0267031 A1 | 11/2007 | Hon | |
| 2008/0257367 A1 | 10/2008 | Paterno | |
| 2009/0126745 A1 | 5/2009 | Hon | |

(56) References Cited

U.S. PATENT DOCUMENTS

| | | |
|---|---|---|
| 2012/0090630 A1 | 4/2012 | Hon |
| 2012/0111347 A1 | 5/2012 | Hon |
| 2014/0261408 A1 | 9/2014 | Depiano et al. |
| 2015/0181943 A1 | 7/2015 | Li et al. |
| 2017/0049156 A1 | 2/2017 | Wang |

FOREIGN PATENT DOCUMENTS

| | | |
|---|---|---|
| CN | 1196660 A | 10/1998 |
| CN | 2293957 Y | 10/1998 |
| CN | 1233436 | 11/1999 |
| CN | 1530041 | 9/2004 |
| CN | 1541577 A | 11/2004 |
| CN | 2719043 Y | 8/2005 |
| CN | 201067079 Y | 6/2008 |
| CN | 201085044 Y | 7/2008 |
| CN | 201797997 U | 4/2011 |
| CN | 202026802 U | 9/2011 |
| CN | 202026804 U | 9/2011 |
| EP | 0342538 A | 11/1989 |
| EP | 0430559 | 6/1991 |
| EP | 0295122 A | 1/1992 |
| EP | 0295122 B1 | 1/1992 |
| EP | 0845220 | 6/1998 |
| EP | 1618803 A | 1/2006 |
| GB | 588117 | 5/1947 |
| GB | 1528391 A | 10/1978 |
| JP | 64-000498 U | 1/1989 |
| JP | 02-124082 A | 5/1990 |
| JP | 06-114105 A | 4/1994 |
| JP | 07-506999 T | 8/1995 |
| JP | 09-075058 A | 3/1997 |
| JP | H9-326299 A | 12/1997 |
| JP | 2984657 | 4/1999 |
| JP | 2001-291598 A | 10/2001 |
| KR | 20020067473 A | 8/2002 |
| UA | 47514 C2 | 7/2002 |
| UA | 49831 | 5/2010 |
| WO | WO1997048293 | 12/1997 |
| WO | WO2000028843 | 5/2000 |
| WO | WO2000049901 A2 | 8/2000 |
| WO | WO2000050111 | 8/2000 |
| WO | WO2001021319 A | 3/2001 |
| WO | WO2002098389 | 12/2002 |
| WO | WO2003034847 | 1/2003 |
| WO | WO2003016783 | 2/2003 |
| WO | WO2003022364 A | 3/2003 |
| WO | WO2003055486 A | 7/2003 |
| WO | WO2003096761 | 11/2003 |
| WO | WO2003101454 | 12/2003 |
| WO | WO2004080216 A1 | 9/2004 |
| WO | WO2004095955 A1 | 11/2004 |
| WO | WO2007131450 | 11/2007 |

OTHER PUBLICATIONS

Australian Patent Office, "Examiner's First Report on Australian Patent Application No. 2004234199", dated Aug. 14, 2009, 3 pages.
Canadian Intellectual Property Office, "Office Action for Canadian Patent Application No. 2,518,174", dated Apr. 14, 2010, 4 pages.
Canadian Intellectual Property Office, "Office Action for Canadian Patent Application No. 2,752,134", dated Feb. 1, 2013, 3 pages.
Canadian Intellectual Property Office, "Office Action for Canadian Patent Application No. 2,752,134", dated Dec. 12, 2013, 2 pages.
Collins, John M. Expert Report—Invalidity (Excerpts), CV14-01645, Jun. 18, 2015.
Collins, John M. Expert Report—Invalidity, CV14-01645-Appendix L-'239, Jun. 18, 2015.
Collins, John M. Expert Report—Invalidity, CV14-01645-Appendix M-1-'641, Jun. 18, 2015.
Collins, John M. Expert Report—Invalidity, CV14-01645-Appendix M-2-'641, Jun. 18, 2015.
Collins, John M. Expert Report—Invalidity, CV14-01645-Appendix M-3-'641, Jun. 18, 2015.
Collins, John M., Expert Report—Invalidity, CV14-01645-Appendix M-4-'641, Jun. 18, 2015.
Eurasian Patent Office, "Translation of Office Action for Eurasian Patent Application No. 200501704", dated Mar. 16, 2007, 1 page.
European Patent Office, "Supplementary European Search Report for European Patent Application No. 04718242", dated Jul. 27, 2007, 3 pages.
European Patent Office, "Supplementary Partial European Search Report for European Patent Application No. 04718242", dated May 22, 2007.
Government of India Patent Office, "First Examination Report for Indian Patent Application No. 3794/DELNP/2005", dated Dec. 18, 2007, 2 pages.
Hewlett-Packard, Thermal Ink-Jet Print Cartridge Designers Guide (2nd Edition), available at least as early as Jan. 12, 1995.
Israel Patent Office, "Hebrew Language Office Action for Israeli Patent Application No. 170872", dated May 22, 2008, 1 page.
ITC Limited, Application for Revocation of Indian Patent No. 228696, served on Applicant's Indian Counsel May 26, 2016 (filed Jul. 27, 2015).
ITC Limited, Application for Revocation of Indian Patent No. 228696, Exhibit EA1—certified impugned patent No. 228696, Jul. 27, 2015.
ITC Limited, Application for Revocation of Indian Patent No. 228696, Exhibit EA2—prosecution history of patent No. 228696, Jul. 27, 2015.
ITC Limited, Application for Revocation of Indian Patent No. 228696, Exhibit EA3—extract of register of patent No. 228696, Jul. 27, 2015.
ITC Limited, Application for Revocation of Indian Patent No. 228696, Exhibit EA4—U.S. Pat. No. 6,196,218, Jul. 27, 2015.
ITC Limited, Application for Revocation of Indian Patent No. 228696, Exhibit EA5—WO200121319, Jul. 27, 2015.
ITC Limited, Application for Revocation of Indian Patent No. 228696, Exhibit EA6—U.S. Pat. No. 3,832,579, Jul. 27, 2015.
ITC Limited, Application for Revocation of Indian Patent No. 228696, Exhibit EA7—U.S. Pat. No. 4,878,107, Jul. 27, 2015.
ITC Limited, Application for Revocation of Indian Patent No. 228696, Exhibit EA8—Form 3, Jul. 27, 2015.
ITC Limited, Application for Revocation of Indian Patent No. 228696, Exhibit EA9—Bibliographic details of corresponding PCT/CN2004/000182, Jul. 27, 2015.
ITC Limited, Application for Revocation of Indian Patent No. 228696, Exhibit EA10—INPADOC family status, Jul. 27, 2015.
ITC Limited, Application for Revocation of Indian Patent No. 228696, Exhibit EA11—pages from prosecution history of counterpart EP patent EP1618803, Jul. 27, 2015.
ITC Limited, Application for Revocation of Indian Patent No. 228696, Exhibit EA12—bibliographic details and legal status of the corresponding Korean Patent Application, Jul. 27, 2015.
Japanese Patent Office, "Office Action for Japanese Patent Application No. 2006-504199 with English translation", dated Oct. 30, 2009, 12 pages.
Korean Intellectual Property Office, "Notice of Preliminary Rejection for Korean Patent Application No. 10-2005-7009767 with English translation", dated Jul. 27, 2009, 13 pages.
Macau Patent Office, "Office Action and Search Report for Macau Patent Application No. I/121", dated Apr. 17, 2009, 14 pages.
Malaysia Intellectual Property Office, "Examiner's Report for Malaysian Patent Application No. PI20041407", dated Sep. 28, 2007, 2 pages.
Mexican Institute of Intellectual Property, "Spanish Language Office Letter for Mexican Patent Application No. PA/a/2005/009191", dated May 8, 2008, 2 pages.
NJOY, Inc. and related Defendants, Defendants' Invalidity Contentions, filed in Fontem v. NJOY, Inc. Consolidated Case No. CV 14-01645 GW (CD Cal) and Related Consolidated Cases, Feb. 26, 2015.
NJOY, Inc. and related Defendants, Exhibit A to Defendants' Invalidity Contentions—Invalidity Claim Chart for U.S. Pat. No. 8,910,641, Feb. 26, 2015.

(56) References Cited

OTHER PUBLICATIONS

NJOY, Inc. and related Defendants, Exhibit C to Defendants' Invalidity Contentions—Invalidity Claim Chart for U.S. Pat. No. 8,899,239, Feb. 26, 2015.

NJOY, Inc. et al., Petition for Inter Partes Review of U.S. Pat. No. 8,899,239—IPR2015-01304, May 29, 2015.

NJOY, Inc. et al., Petition for Inter Partes Review of U.S. Pat. No. 8,899,239—IPR2015-01304, Ex. 1001, U.S. Pat. No. 8,899,239, May 29, 2015.

NJOY, Inc. et al., Petition for Inter Partes Review of U.S. Pat. No. 8,899,239—IPR2015-01304, Ex. 1002, Declaration Dr. Samir Nayfeh, Ph.D. ("Nayfeh Decl."), May 29, 2015.

NJOY, Inc. et al., Petition for Inter Partes Review of U.S. Pat. No. 8,899,239—IPR2015-01304, Ex. 1003, Chinese Patent Publication No. 1233436A ("Hongbin"), May 29, 2015.

NJOY, Inc. et al., Petition for Inter Partes Review of U.S. Pat. No. 8,899,239—IPR2015-01304, Ex. 1004, U.S. Pat. No. 5,819,756 ("Mielordt"), May 29, 2015.

NJOY, Inc. et al., Petition for Inter Partes Review of U.S. Pat. No. 8,899,239—IPR2015-01304, Ex. 1005, U.S. Pat. No. 6,234,167 ("Cox"), May 29, 2015.

NJOY, Inc. et al., Petition for Inter Partes Review of U.S. Pat. No. 8,899,239—IPR2015-01304, Ex. 1006, European Patent Publication No. 0845220 A1 ("Suss"), May 29, 2015.

NJOY, Inc. et al., Petition for Inter Partes Review of U.S. Pat. No. 8,899,239—IPR2015-01304, Ex. 1007, U.S. Pat. No. 6,196,218 ("Voges"), May 29, 2015.

NJOY, Inc. et al., Petition for Inter Partes Review of U.S. Pat. No. 8,899,239—IPR2015-01304, Ex. 1008, Fontem Ventures, B.V., et al. v. NJOY, Inc. et al., Civ. No. 14-1645 Dkt. 133 (CD. Cal. May 7, 2015) (Markman Hearing/Claim Construction Order), May 29, 2015.

NJOY, Inc. et al., Petition for Inter Partes Review of U.S. Pat. No. 8,899,239—IPR2015-01304, Ex. 1009, *Fontem Ventures, B.V., et al. v. NJOY, Inc. et al.*, Civ. No. 14-1645 Dkt. 65 (CD. Cal. Jan. 29, 2015) (Rulings on Claim Construction), May 29, 2015.

NJOY, Inc. et al., Petition for Inter Partes Review of U.S. Pat. No. 8,899,239—IPR2015-01304, Ex. 1010, *Fontem Ventures, B.V., et al. v. NJOY, Inc. et al.*, Civ. No. 14/1645 Dkt. 93 (CD. Cal. Mar. 19, 2015) (Joint Claim Construction and Prehearing Statement), May 29, 2015.

NJOY, Inc. et al., Petition for Inter Partes Review of U.S. Pat. No. 8,899,239—IPR2015-01304, Ex. 1011, *Fontem Ventures, B.V., et al. v. NJOY, Inc. et al.*, Civ. No. 14/1645 Dkt. 34 (CD. Cal. Sep. 30, 2014) (Revised Joint Claim Construction and Prehearing Statement), May 29, 2015.

NJOY, Inc. et al., Petition for Inter Partes Review of U.S. Pat. No. 8,899,239—IPR2015-01304, Ex. 1012, Patent Owner's Dictionary Definitions of "E-Cigarette" from related IPR proceedings, May 29, 2015).

NJOY, Inc. et al., Petition for Inter Partes Review of U.S. Pat. No. 8,899,239—IPR2015-01304, Ex. 1013, *Fontem Ventures, B.V., et al. v. NJOY, Inc. et al.*, Civ. No. 14-1645 Dkt. 95 (CD. Cal. Apr. 9, 2015) (Defendant's Opening Claim Construction Brief), May 29, 2015.

NJOY, Inc. et al., Petition for Inter Partes Review of U.S. Pat. No. 8,899,239—IPR2015-01304, Ex. 1014, *Fontem Ventures, B.V., et al. v. NJOY, Inc. et al.*, Civ. No. 14-1645 Dkt. 116 (CD. Cal. Apr. 23, 2015) (Defendant's Responsive Claim Construction Brief), May 29, 2015.

NJOY, Inc. et al., Petition for Inter Partes Review of U.S. Pat. No. 8,899,239—IPR2015-01304, Ex. 1015, *Fontem Ventures, B.V., et al. v. NJOY, Inc. et al.*, Civ. No. 14/1645 Dkt. 117 (CD. Cal. Apr. 23, 2015) (Plaintiffs' Responsive Claim Construction Brief), May 29, 2015.

NJOY, Inc. et al., Petition for Inter Partes Review of U.S. Pat. No. 8,899,239—IPR2015-01304, Ex. 1016, *Fontem Ventures, B.V., et al. v. NJOY, Inc. et al.*, Civ. No. 14/1645 Dkt. 117-2 (CD. Cal. Apr. 23, 2015) (Plaintiffs' Responsive Claim Construction Brief Exhibit 3), May 29, 2015.

NJOY, Inc. et al., Petition for Inter Partes Review of U.S. Pat. No. 8,899,239—IPR2015-01304, Ex. 1017, *Fontem Ventures, B.V., et al. v. NJOY, Inc. et al.*, Civ. No. 14/1645 Dkt. 117-2 (CD. Cal. Apr. 23, 2015) (Plaintiffs' Responsive Claim Construction Brief Exhibit 4), May 29, 2015.

NJOY, Inc. et al., Petition for Inter Partes Review of U.S. Pat. No. 8,899,239—IPR2015-01304, Ex. 1018, *Fontem Ventures, B.V., et al. v. NJOY, Inc. et al.*, Civ. No. 14/1645 Dkt. 117-2 (CD. Cal. Apr. 23, 2015) (Plaintiffs' Responsive Claim Construction Brief Exhibit 5), May 29, 2015.

NJOY, Inc. et al., Petition for Inter Partes Review of U.S. Pat. No. 8,899,239—IPR2015-01304, Ex. 1019, Declaration of Saurabh Gupta from IPR2014-01289, May 29, 2015.

NJOY, Inc. et al., Petition for Inter Partes Review of U.S. Pat. No. 8,899,239—IPR2015-01304, Ex. 1020, Curriculum Vitae of Dr. Samir Nayfeh, Ph.D., May 29, 2015.

NJOY, Inc. et al., Petition for Inter Partes Review of U.S. Pat. No. 8,899,239—IPR2015-01304, Ex. 1021, Abstract of Title for U.S. Pat. No. 6,234,167 ("Cox"), May 29, 2015.

NJOY, Inc. et al., Petition for Inter Partes Review of U.S. Pat. No. 8,899,239—IPR2015-01304, Ex. 1022, U.S. Pat. No. 5,666,977 ("Higgins"), May 29, 2015.

NJOY, Inc. et al., Petition for Inter Partes Review of U.S. Pat. No. 8,899,239—IPR2015-01304, Ex. 1023, U.S. Pat. No. 6,155,268 ("Takeuchi"), May 29, 2015.

NJOY, Inc. et al., Petition for Inter Partes Review of U.S. Pat. No. 8,899,239—IPR2015-01304, Ex. 1024, U.S. Pat. No. 5,505,214 ("Collins"), May 29, 2015.

NJOY, Inc. et al., Petition for Inter Partes Review of U.S. Pat. No. 8,899,239—IPR2015-01304, Ex. 1025, U.S. Pat. No. 2,545,851 ("Kardos"), May 29, 2015.

NJOY, Inc. et al., Petition for Inter Partes Review of U.S. Pat. No. 8,899,239—IPR2015-01304, Ex. 1026, U.S. Pat. No. 3,479,561 ("Janning"), May 29, 2015.

NJOY, Inc. et al., Petition for Inter Partes Review of U.S. Pat. No. 8,899,239—IPR2015-01304, Ex. 1027, U.S. Pat. No. 4,771,796 ("Myer"), May 29, 2015.

NJOY, Inc. et al., Petition for Inter Partes Review of U.S. Pat. No. 8,899,239—IPR2015-01304, Ex. 1028, U.S. Pat. No. 6,719,443 ("Gutstein"), May 29, 2015.

NJOY, Inc. et al., Petition for Inter Partes Review of U.S. Pat. No. 8,899,239—IPR2015-01304, Ex. 1029, U.S. Pat. No. 5,388,574 ("Ingebrethsen"), May 29, 2015.

NJOY, Inc. et al., Petition for Inter Partes Review of U.S. Pat. No. 8,910,641—IPR2015-01299, May 29, 2015.

NJOY, Inc. et al., Petition for Inter Partes Review of U.S. Pat. No. 8,910,641—IPR2015-01299, Ex. 1001, U.S. Pat. No. 8,910,641 ("The '641 patent"), May 29, 2015.

NJOY, Inc. et al., Petition for Inter Partes Review of U.S. Pat. No. 8,910,641—IPR2015-01299, Ex. 1002, Declaration Dr. Samir Nayfeh, Ph.D. ("Nayfeh Decl."), May 29, 2015.

NJOY, Inc. et al., Petition for Inter Partes Review of U.S. Pat. No. 8,910,641—IPR2015-01299, Ex. 1003, U.S. Pat. No. 6,155,268 ("Takeuchi"), May 29, 2015.

NJOY, Inc. et al., Petition for Inter Partes Review of U.S. Pat. No. 8,910,641—IPR2015-01299, Ex. 1004, U.S. Pat. No. 5,666,977 ("Higgins"), May 29, 2015.

NJOY, Inc. et al., Petition for Inter Partes Review of U.S. Pat. No. 8,910,641—IPR2015-01299, Ex. 1005, U.S. Pat. No. 3,200,819 ("Gilbert"), May 29, 2015.

NJOY, Inc. et al., Petition for Inter Partes Review of U.S. Pat. No. 8,910,641—IPR2015-01299, Ex. 1006, U.S. Pat. No. 5,388,574 ("Ingebrethsen"), May 29, 2015.

NJOY, Inc. et al., Petition for Inter Partes Review of U.S. Pat. No. 8,910,641—IPR2015-01299, Ex. 1007, U.S. Pat. No. 4,207,457 ("Haglund"), May 29, 2015.

NJOY, Inc. et al., Petition for Inter Partes Review of U.S. Pat. No. 8,910,641—IPR2015-01299, Ex. 1008, U.S. Pat. No. 5,743,251, May 29, 2015.

NJOY, Inc. et al., Petition for Inter Partes Review of U.S. Pat. No. 8,910,641—IPR2015-01299, Ex. 1009, U.S. Publication No. 2015/0020825, May 29, 2015.

(56) References Cited

OTHER PUBLICATIONS

NJOY, Inc. et al., Petition for Inter Partes Review of U.S. Pat. No. 8,910,641—IPR2015-01299, Ex. 1010, European Publication No. 0 845 220 Al ("Susa"), May 29, 2015.
NJOY, Inc. et al., Petition for Inter Partes Review of U.S. Pat. No. 8,910,641—IPR2015-01299, Ex. 1011, *Fontem Ventures, B.V., et al. v. NJOY, Inc. et al.*, Civ. No. 14/1645 Dkt. 133 (C.D. Cal. May 7, 2015) (Markman Hearing/Claim Construction Order), May 29, 2015.
NJOY, Inc. et al., Petition for Inter Partes Review of U.S. Pat. No. 8,910,641—IPR2015-01299, Ex. 1012, *Fontem Ventures, B.V., et al. v. NJOY, Inc. et al.*, Civ. No. 14-1645 Dkt. 65 (C.D. Cal. Jan. 29, 2015) (Rulings on Claim Construction), May 29, 2015.
NJOY, Inc. et al., Petition for Inter Partes Review of U.S. Pat. No. 8,910,641—IPR2015-01299, Ex. 1013, *Fontem Ventures, B.V., et al. v. NJOY, Inc. et al.*, Civ. No. 14-1645 Dkt. 93 (C.D. Cal. Mar. 19, 2015) (Joint Claim Construction and Prehearing Statement), May 29, 2015.
NJOY, Inc. et al., Petition for Inter Partes Review of U.S. Pat. No. 8,910,641—IPR2015-01299, Ex. 1014, *Fontem Ventures, B.V., et al. v. NJOY, Inc. et al.*, Civ. No. 14-1645 Dkt. 34 (C.D. Cal. Sep. 30, 2014) (Revised Joint Claim Construction and Prehearing Statement), May 29, 2015.
NJOY, Inc. et al., Petition for Inter Partes Review of U.S. Pat. No. 8,910,641—IPR2015-01299, Ex. 1015, Patent Owner's Dictionary Definitions of "E-Cigarette" from related IPR proceedings, May 29, 2015.
NJOY, Inc. et al., Petition for Inter Partes Review of U.S. Pat. No. 8,910,641—IPR2015-01299, Ex. 1016, U.S. Pat. No. 6,196,218, May 29, 2015.
NJOY, Inc. et al., Petition for Inter Partes Review of U.S. Pat. No. 8,910,641—IPR2015-01299, Ex. 1017, U.S. Pat. No. 5,144,962, May 29, 2015.
NJOY, Inc. et al., Petition for Inter Partes Review of U.S. Pat. No. 8,910,641—IPR2015-01299, Ex. 1018, '641 Patent File History, Final Rejection (Aug. 28, 2014), May 29, 2015.
NJOY, Inc. et al., Petition for Inter Partes Review of U.S. Pat. No. 8,910,641—IPR2015-01299, Ex. 1019, Curriculum Vitae of Dr. Samir Nayfeh, Ph.D., May 29, 2015.
NJOY, Inc. et al., Petition for Inter Partes Review of U.S. Pat. No. 8,910,641—IPR2015-01299, Ex. 1020, Abstract of Title for U.S. Pat. No. 5,388,574, May 29, 2015.
Nu Mark LLC, Answer to Complaint and Counterclaims in *Fontem Ventures B.V. v. Nu Mark LLC*, 16-CV-2291, Dkt. 025, Jun. 27, 2016.
Nu Mark LLC, Answer to Complaint and Counterclaims in *Fontem Ventures B.V. v. Nu Mark LLC*, 16-CV-1259, Dkt. 034, Oct. 26, 2016.
Nu Mark LLC, First Amended Answer and Counterclaims in *Fontem Ventures B.V. v. Nu Mark LLC*, 16-CV-2291, Dkt. 042, Jul. 28, 2016.
Nu Mark LLC, IPR2016-01668, Ex.1001 U.S. Pat. No. 9,364,027 (the "027 Patent").
Nu Mark LLC, IPR2016-01668, Ex.1002 File History for U.S. Pat. No. 9,364,027.
Nu Mark LLC, IPR2016-01668, Ex.1003 Declaration of John M. Collins, Ph.D.
Nu Mark LLC, IPR2016-01668, Ex.1004 Curriculum Vitae of Dr. John M. Collins.
Nu Mark LLC, IPR2016-01668, Ex.1005 U.S. Pat. App. Pub. No. 2006/0196518 A1 ("Hon 518").
Nu Mark LLC, IPR2016-01668, Ex.1006 File History for U.S. Appl. No. 13/088,276 (issued as U.S. Pat. No. 8,511,318).
Nu Mark LLC, IPR2016-01668, Ex.1007 Blackline Specification filed in U.S. Appl. No. 10/547,244 on Jan. 20, 2012.
Nu Mark LLC, IPR2016-01668, Ex.1008 Canadian Patent Appl. No. 2,752,134 ("Hon 134").
Nu Mark LLC, IPR2016-01668, Ex.1009 *Fontem Ventures, B.V., et al. v. NJOY, Inc. et al.*, Case 2:14-cv-01645-GW(MRWx), Dkt. 358 (C.D. Cal. Oct. 22, 2015).
Nu Mark LLC, IPR2016-01668, Ex.1010 Originally filed Abstract, Specification, Drawings, and Claims of U.S. Appl. No. 10/547,244 (submitted Aug. 26, 2005).
Nu Mark LLC, IPR2016-01668, Ex.1011 Certified Translation of WO 2004/095955.
Nu Mark LLC, IPR2016-01668, Ex.1012 U.S. Pat. No. 8,910,641.
Nu Mark LLC, IPR2016-01668, Ex.1013 Patent Owner Preliminary Response in IPR2015-01604.
Nu Mark LLC, IPR2016-01668, Ex.1014 Patent Owner Preliminary Response in IPR2015-01301.
Nu Mark LLC, IPR2016-01668, Ex.1015 Patent Owner Preliminary Response in IPR2015-01513.
Nu Mark LLC, IPR2016-01668, Ex.1016 Originally filed Abstract, Specification, Drawings, and Claims of U.S. Appl. No. 13/548,659.
Nu Mark LLC, IPR2016-01668, Ex.1017 Originally filed Abstract, Specification, Drawings, and Claims of U.S. Appl. No. 13/921,582.
Nu Mark LLC, IPR2016-01668, Ex.1018 Originally filed Abstract, Specification, Drawings, and Claims of U.S. Appl. No. 14/289,366.
Nu Mark LLC, Petition for Inter Partes Review of U.S. Pat. No. 8,889,239—IPR2016-01302, Paper 1, Jun. 28, 2016.
Nu Mark LLC, Petition for Inter Partes Review of U.S. Pat. No. 8,889,239—IPR2016-01302, Ex. 1001 U.S. Pat. No. 8,899,239 ("The 239 Patent"), Jun. 28, 2016.
Nu Mark LLC, Petition for Inter Partes Review of U.S. Pat. No. 8,889,239—IPR2016-01302, Ex. 1002 File History for U.S. Pat. No. 8,899,239, Jun. 28, 2016.
Nu Mark LLC, Petition for Inter Partes Review of U.S. Pat. No. 8,889,239—IPR2016-01302, Ex. 1003 Declaration of Dr. John M. Collins (Collins Decl.), Jun. 28, 2016.
Nu Mark LLC, Petition for Inter Partes Review of U.S. Pat. No. 8,889,239—IPR2016-01302, Ex. 1004 U.S. Pat. No. 3,479,561 ("Janning"), Jun. 28, 2016.
Nu Mark LLC, Petition for Inter Partes Review of U.S. Pat. No. 8,889,239—IPR2016-01302, Ex. 1005 U.S. Patent Publication No. 2004/0149282 ("Hickle"), Jun. 28, 2016.
Nu Mark LLC, Petition for Inter Partes Review of U.S. Pat. No. 8,889,239—IPR2016-01302, Ex. 1006 Certified Translation of Chinese Utility Model Publication No. CN1233436A ("Hongbin Translation"), Jun. 28, 2016.
Nu Mark LLC, Petition for Inter Partes Review of U.S. Pat. No. 8,889,239—IPR2016-01302, Ex. 1007 Chinese Utility Model Publication No. CN 1233436A ("Hongbin"), Jun. 28, 2016.
Nu Mark LLC, Petition for Inter Partes Review of U.S. Pat. No. 8,889,239—IPR2016-01302, Ex. 1008 Fontem's Opening Supplemental Brief Regarding "Electronic Cigarette", Case No. CV14-1645 GW (MRWx) (N.D. Cal. Nov. 5, 2015), D.I. 370, Jun. 28, 2016.
Nu Mark LLC, Petition for Inter Partes Review of U.S. Pat. No. 8,889,239—IPR2016-01302, Ex. 1009 U.S. Appl. No. 60/430,088 ("The '088 Provisional"), Jun. 28, 2016.
Nu Mark LLC, Petition for Inter Partes Review of U.S. Pat. No. 8,889,239—IPR2016-01302, Ex. 1010 U.S. Pat. No. 6,285,017 ("Brickell"), Jun. 28, 2016.
Nu Mark LLC, Petition for Inter Partes Review of U.S. Pat. No. 8,889,239—IPR2016-01302, Ex. 1011 U.S. Pat. No. 6,690,121 ("Weindorf"), Jun. 28, 2016.
Nu Mark LLC, Petition for Inter Partes Review of U.S. Pat. No. 8,889,239—IPR2016-01302, Ex. 1012 U.S. Pat. No. 5,819,756 ("Mielordt"), Jun. 28, 2016.
Nu Mark LLC, Petition for Inter Partes Review of U.S. Pat. No. 8,889,239—IPR2016-01302, Ex. 1013 U.S. Patent Publication No. 2006/0093977 ("Pellizzari I"), Jun. 28, 2016.
Nu Mark LLC, Petition for Inter Partes Review of U.S. Pat. No. 8,889,239—IPR2016-01302, Ex. 1014 U.S. Pat. No. 7,059,307 ("Pellizzari II"), Jun. 28, 2016.
Nu Mark LLC, Petition for Inter Partes Review of U.S. Pat. No. 8,889,239—IPR2016-01302, Ex. 1015 U.S. Pat. No. 5,894,841 ("Voges"), Jun. 28, 2016.
Nu Mark LLC, Petition for Inter Partes Review of U.S. Pat. No. 8,889,239—IPR2016-01302, Ex. 1016 U.S. Pat. No. 5,743,251 ("Howell"), Jun. 28, 2016.

(56) References Cited

OTHER PUBLICATIONS

Nu Mark LLC, Petition for Inter Partes Review of U.S. Pat. No. 8,889,239—IPR2016-01302, Ex. 1017 U.S. Pat. No. 6,501,052 ("Cox"), Jun. 28, 2016.
Nu Mark LLC, Petition for Inter Partes Review of U.S. Pat. No. 8,889,239—IPR2016-01302, Ex. 1018 U.S. Pat. No. 6,491,233 ("Nichols"), Jun. 28, 2016.
Nu Mark LLC, Petition for Inter Partes Review of U.S. Pat. No. 9,364,027—IPR2016-01668, Aug. 24, 2016.
Nu Mark LLC, Petition for Inter Partes Review of U.S. Pat. No. 9,364,027—IPR2017-00304, Paper 1 Petition, Nov. 18, 2016.
Nu Mark LLC, Petition for Inter Partes Review of U.S. Pat. No. 9,364,027—IPR2017-00304, Ex.1001 U.S. Pat. No. 9,364,027 (the "027 Patent"), Nov. 18, 2016.
Nu Mark LLC, Petition for Inter Partes Review of U.S. Pat. No. 9,364,027—IPR2017-00304, Ex.1002 File History for U.S. Pat. No. 9,364,027 (excerpts), Nov. 18, 2016.
Nu Mark LLC, Petition for Inter Partes Review of U.S. Pat. No. 9,364,027—IPR2017-00304, Ex.1003 Declaration of Dr. John M. Collins ("Collins Decl."), Nov. 18, 2016.
Nu Mark LLC, Petition for Inter Partes Review of U.S. Pat. No. 9,364,027—IPR2017-00304, Ex.1004 Certified Translation of Chinese Utility Model Publication No. CN 1233436A ("Hongbin Translation"), Nov. 18, 2016.
Nu Mark LLC, Petition for Inter Partes Review of U.S. Pat. No. 9,364,027—IPR2017-00304, Ex.1005 Chinese Utility Model Publication No. CN 1233436A ("Hongbin"), Nov. 18, 2016.
Nu Mark LLC, Petition for Inter Partes Review of U.S. Pat. No. 9,364,027—IPR2017-00304, Ex.1006 U.S. Patent Publication No. 2004/0149282 ("Hickle"), Nov. 18, 2016.
Nu Mark LLC, Petition for Inter Partes Review of U.S. Pat. No. 9,364,027—IPR2017-00304, Ex.1007 U.S. Appl. No. 60/430,088 ("The 088 provisional") to Hickle, Nov. 18, 2016.
Nu Mark LLC, Petition for Inter Partes Review of U.S. Pat. No. 9,364,027—IPR2017-00304, Ex.1008 U.S. Pat. No. 1,147,416 ("MacDonald"), Nov. 18, 2016.
Nu Mark LLC, Petition for Inter Partes Review of U.S. Pat. No. 9,364,027—IPR2017-00304, Ex.1009 U.S. Pat. No. 5,666,977 ("Higgins"), Nov. 18, 2016.
Nu Mark LLC, Petition for Inter Partes Review of U.S. Pat. No. 9,364,027—IPR2017-00304, Ex.1010 U.S. Pat. No. 6,285,017 ("Brickell"), Nov. 18, 2016.
Nu Mark LLC, Petition for Inter Partes Review of U.S. Pat. No. 9,364,027—IPR2017-00304, Ex.1011 U.S. Pat. No. 6,690,121 ("Weindorf"), Nov. 18, 2016.
Nu Mark LLC, Petition for Inter Partes Review of U.S. Pat. No. 9,364,027—IPR2017-00304, Ex.1012 U.S. Pat. No. 5,743,251 ("Howell"), Nov. 18, 2016.
Nu Mark LLC, Petition for Inter Partes Review of U.S. Pat. No. 9,364,027—IPR2017-00304, Ex.1013 U.S. Pat. No. 6,598,607 ("Adiga"), Nov. 18, 2016.
Nu Mark LLC, Petition for Inter Partes Review of U.S. Pat. No. 9,364,027—IPR2017-00304, Ex.1014 U.S. Pat. No. 1,514,682 ("Wilson"), Nov. 18, 2016.
Nu Mark LLC, Petition for Inter Partes Review of U.S. Pat. No. 9,364,027—IPR2017-00304, Ex.1015 U.S. Pat. No. 2,057,353 ("Whittemore"), Nov. 18, 2016.
Nu Mark LLC, Petition for Inter Partes Review of U.S. Pat. No. 9,364,027—IPR2017-00304, Ex.1016 U.S. Pat. No. 4,947,874 ("Brooks"), Nov. 18, 2016.
Nu Mark LLC, Petition for Inter Partes Review of U.S. Pat. No. 9,364,027—IPR2017-00304, Ex.1017 U.S. Pat. No. 3,479,561 ("Janning"), Nov. 18, 2016.
Nu Mark LLC, Petition for Inter Partes Review of U.S. Pat. No. 9,364,027—IPR2017-00304, Ex.1018 U.S. Pat. No. 5,894,841 ("Voges"), Nov. 18, 2016.
Nu Mark LLC, Petition for Inter Partes Review of U.S. Pat. No. 9,364,027—IPR2017-00304, Ex.1019 U.S. Pat. No. 6,491,233 ("Nichols"), Nov. 18, 2016.
Nu Mark LLC, Petition for Inter Partes Review of U.S. Pat. No. 9,364,027—IPR2017-00304, Ex.1020 U.S. Pat. No. 1,347,631 ("Jean"), Nov. 18, 2016.
Nu Mark LLC, Petition for Inter Partes Review of U.S. Pat. No. 9,364,027—IPR2017-00304, Ex.1021 U.S. Pat. No. 2,140,516 ("Cowan"), Nov. 18, 2016.
Nu Mark LLC, Petition for Inter Partes Review of U.S. Pat. No. 9,364,027—IPR2017-00304, Ex.1022 U.S. Pat. No. 3,651,240 ("Kirkpatrick"), Nov. 18, 2016.
Nu Mark LLC, Petition for Inter Partes Review of U.S. Pat. No. 9,364,027—IPR2017-00304, Ex.1023 U.S. Pat. No. 2,896,856 ("Kravits"), Nov. 18, 2016.
Nu Mark LLC, Petition for Inter Partes Review of U.S. Pat. No. 9,364,027—IPR2017-00304, Ex.1024 Citing References for U.S. Pat. No. 2,896,856, Nov. 18, 2016.
Nu Mark LLC, Petition for Inter Partes Review of U.S. Pat. No. 9,364,027—IPR2017-00304, Ex.1025 U.S. Pat. No. 5,400,969 ("Keene"), Nov. 18, 2016.
Nu Mark LLC, Petition for Inter Partes Review of U.S. Pat. No. 9,364,027—IPR2017-00304, Ex.1026 Citing References for U.S. Pat. No. 5,400,969, Nov. 18, 2016.
Nu Mark LLC, Petition for Inter Partes Review of U.S. Pat. No. 9,364,027—IPR2017-00304, Ex.1027 U.S. Pat. No. 5,732,685 ("Nakamura"), Nov. 18, 2016.
Nu Mark LLC, Petition for Inter Partes Review of U.S. Pat. No. 9,364,027—IPR2017-00304, Ex.1028 Citing References for U.S. Pat. No. 5,732,685, Nov. 18, 2016.
Nu Mark LLC, Petition for Inter Partes Review of U.S. Pat. No. 9,364,027—IPR2017-00304, Ex.1029 U.S. Patent Publication No. 2005/0115243 ("Adle"), Nov. 18, 2016.
Nu Mark LLC, Petition for Inter Partes Review of U.S. Pat. No. 9,364,027—IPR2017-00304, Ex.1030 References Cited for U.S. Patent Publication No. 2005/0115243, Nov. 18, 2016.
Nu Mark LLC, Petition for Inter Partes Review of U.S. Pat. No. 9,364,027—IPR2017-00304, Ex.1031 McGraw-Hill Dictionary of Scientific and Technical Terms, McGraw-Hill Companies, Inc., (3rd ed. 1984) (excerpts), Nov. 18, 2016.
Nu Mark LLC, Petition for Inter Partes Review of U.S. Pat. No. 9,364,027—IPR2017-00304, Ex.1032 U.S. Pat. No. 3,933,643 ("Colvin"), Nov. 18, 2016.
Nu Mark LLC, Petition for Inter Partes Review of U.S. Pat. No. 9,364,027—IPR2017-00304, Ex.1033 U.S. Pat. No. 6,476,151 ("Araki"), Nov. 18, 2016.
Nu Mark LLC, Petition for Inter Partes Review of U.S. Pat. No. 9,364,027—IPR2017-00304, Ex.1034 U.S. Patent Publication No. 2006/0093977 A1 ("Pellizzari I"), Nov. 18, 2016.
Nu Mark LLC, Petition for Inter Partes Review of U.S. Pat. No. 9,364,027—IPR2017-00304, Ex.1035 U.S. Pat. No. 7,059,307 ("Pellizzari II"), Nov. 18, 2016.
Nu Mark LLC, Petition for Inter Partes Review of U.S. Pat. No. 9,364,027—IPR2017-00304, Ex.1036 U.S. Pat. No. 6,501,052 ("Cox"), Nov. 18, 2016.
Nu Mark LLC, Petition for Inter Partes Review of U.S. Pat. No. 9,364,027—IPR2017-00304, Ex.1037 U.S. Pat. No. 438,310 ("Edison"), Nov. 18, 2016.
Nu Mark LLC, Petition for Inter Partes Review of U.S. Pat. No. 9,364,027—IPR2017-00304, Ex.1038 U.S. Pat. No. 3,200,819 ("Gilbert"), Nov. 18, 2016.
Nu Mark LLC, Petition for Inter Partes Review of U.S. Pat. No. 9,364,027—IPR2017-00304, Ex.1039 J.A. Speck, Mechanical Fastening, Joining, and Assembly (1997) (excerpt), Nov. 18, 2016.
Nu Mark LLC, Petition for Inter Partes Review of U.S. Pat. No. 9,364,027—IPR2017-00304, Ex.1040 European Patent Application No. EP0845220 A1 ("Susa"), Nov. 18, 2016.
Nu Mark LLC, Petition for Inter Partes Review of U.S. Pat. No. 9,364,027—IPR2017-00304, Ex.1041 U.S. Pat. No. 2,442,004 ("Hayward-Butt"), Nov. 18, 2016.
Nu Mark LLC, Petition for Inter Partes Review of U.S. Pat. No. 9,364,027—IPR2017-00304, Ex.1042 U.S. Pat. No. 1,775,947 ("Robinson"), Nov. 18, 2016.
Nu Mark LLC, Petition for Inter Partes Review of U.S. Pat. No. 9,364,027—IPR2017-00304, Ex.1043 U.S. Pat. No. 6,155,268 ("Takeuchi"), Nov. 18, 2016.

(56) References Cited

OTHER PUBLICATIONS

R.J. Reynolds Vapor Company, Answer to Complaint in *Fontem Holdings B.V. v. R.J. Reynolds Vapor Company*, 16-CV-2286, Dkt. 027, Jun. 27, 2016.
R.J. Reynolds Vapor Company, First Amended Answer to Complaint in *Fontem Holdings B.V. v. R.J. Reynolds Vapor Company*, 16-CV-2286, Dkt. 033, Jul. 25, 2016.
R.J. Reynolds Vapor Company, IPR2017-01120, U.S. Pat. No. 8,899,239, Exhibit 1001, U.S. Pat. No. 8,899,239 ("The 239 patent"), Apr. 3, 2017.
R.J. Reynolds Vapor Company, IPR2017-01120, U.S. Pat. No. 8,899,239, Exhibit 1002, Chinese Patent Application Publication No. CN1233436A ("Hongbin"), Apr. 3, 2017.
R.J. Reynolds Vapor Company, IPR2017-01120, U.S. Pat. No. 8,899,239, Exhibit 1003, Certified translation of Chinese Patent Application Publication No. CN1233436A ("Hongbin"), Apr. 3, 2017.
R.J. Reynolds Vapor Company, IPR2017-01120, U.S. Pat. No. 8,899,239, Exhibit 1004, Japanese Unexamined Patent Application Publication No. 2001-291598 ("JP598" or "JP98 publication"), Apr. 3, 2017.
R.J. Reynolds Vapor Company, IPR2017-01120, U.S. Pat. No. 8,899,239, Exhibit 1005, Certified translation of Japanese Unexamined Patent Application Publication No. 2001-291598 ("JP598" or "JP98 publication"), Apr. 3, 2017.
R.J. Reynolds Vapor Company, IPR2017-01120, U.S. Pat. No. 8,899,239, Exhibit 1006, U.S. Pat. No. 2,057,353 ("Whittemore"), Apr. 3, 2017.
R.J. Reynolds Vapor Company, IPR2017-01120, U.S. Pat. No. 8,899,239, Exhibit 1007, U.S. Pat. No. 6,155,268 ("Takeuchi") Apr. 3, 2017.
R.J. Reynolds Vapor Company, IPR2017-01120, U.S. Pat. No. 8,899,239, Exhibit 1008, Declaration of Dr. Robert H. Sturges regarding U.S. Pat. No. 8,899,239, Apr. 3, 2017.
R.J. Reynolds Vapor Company, IPR2017-01120, U.S. Pat. No. 8,899,239, Exhibit 1009, IPR2016-01272, Petition for Inter Partes Review, Apr. 3, 2017.
R.J. Reynolds Vapor Company, IPR2017-01120, U.S. Pat. No. 8,899,239, Exhibit 1010, IPR2016-01272, Decision Instituting Inter Partes Review ("Institution Decision"), Apr. 3, 2017.
R.J. Reynolds Vapor Company, IPR2017-01120, U.S. Pat. No. 8,899,239, Exhibit 1011, U.S. Pat. No. 4,947,874 ("Brooks"), Apr. 3, 2017.
R.J. Reynolds Vapor Company, IPR2017-01120, U.S. Pat. No. 8,899,239, Exhibit 1012, Excerpt from Marks' Standard Handbook for Mechanical Engineers (1978), Apr. 3, 2017.
R.J. Reynolds Vapor Company, IPR2017-01120, U.S. Pat. No. 8,899,239, Exhibit 1013, U.S. Pat. No. 6,598,607 ("Adiga"), Apr. 3, 2017.
R.J. Reynolds Vapor Company, IPR2017-01120, U.S. Pat. No. 8,899,239, Exhibit 1014, U.S. Pat. No. 4,793,365 ("Sensabaugh"), Apr. 3, 2017.
R.J. Reynolds Vapor Company, IPR2017-01120, U.S. Pat. No. 8,899,239, Exhibit 1015, U.S. Pat. No. 5,203,355 ("Clearman"), Apr. 3, 2017.
R.J. Reynolds Vapor Company, IPR2017-01120, U.S. Pat. No. 8,899,239, Exhibit 1016, U.S. Pat. No. 2,472,282 ("Burchett"), Apr. 3, 2017.
R.J. Reynolds Vapor Company, IPR2017-01120, U.S. Pat. No. 8,899,239, Exhibit 1017, U.S. Pat. No. 2,032,695 ("Gimera"), Apr. 3, 2017.
R.J. Reynolds Vapor Company, IPR2017-01120, U.S. Pat. No. 8,899,239, Exhibit 1018, U.S. Pat. No. 3,479,561 ("Janning"), Apr. 3, 2017.
R.J. Reynolds Vapor Company, IPR2017-01120, U.S. Pat. No. 8,899,239, Exhibit 1019, Plaintiffs Responsive Claim Construction Brief from *Fontem Ventures, B. V. et al. v. NJOY, Inc. et al*, Case No. 14-cv-1645-GW (MRWx) (C.D. Cal. Apr. 23, 2015) (Dkt No. 117), Apr. 3, 2017.
R.J. Reynolds Vapor Company, IPR2017-01120, U.S. Pat. No. 8,899,239, Exhibit 1020, Ex. 3 attached to Plaintiff's Responsive Claim Construction Brief from *Fontem Ventures, B. V. et al. v. NJOY, Inc. et al*, Case No. 14-cv-1645-GW (MRWx) (C.D. Cal. Apr. 23, 2015) (Dkt No. 117-2), Apr. 3, 2017.
R.J. Reynolds Vapor Company, IPR2017-01120, U.S. Pat. No. 8,899,239, Exhibit 1021, Ex. 4 attached to Plaintiff's Responsive Claim Construction Brief from *Fontem Ventures, B. V. et al. v. NJOY, Inc. et al*, Case No. 14-cv-1645-GW (MRWx) (C.D. Cal. Apr. 23, 2015) (Dkt No. 117-2), Apr. 3, 2017.
R.J. Reynolds Vapor Company, IPR2017-01120, U.S. Pat. No. 8,899,239, Exhibit 1022, Ex. 5 attached to Plaintiff's Responsive Claim Construction Brief from *Fontem Ventures, B. V. et al. v. NJOY, Inc. et al*, Case No. 14-cv-1645-GW (MRWx) (C.D. Cal. Apr. 23, 2015) (Dkt No. 117-2), Apr. 3, 2017.
R.J. Reynolds Vapor Company, IPR2017-01120, U.S. Pat. No. 8,899,239, Exhibit 1023, Mosdesign Semiconductor Corp., Datasheet for M1600 LED Drivers, Apr. 3, 2017.
R.J. Reynolds Vapor Company, IPR2017-01120, U.S. Pat. No. 8,899,239, Exhibit 1024, Excerpt from Merriam-Webster's Collegiate Dictionary, 10th ed. (2002), Apr. 3, 2017.
R.J. Reynolds Vapor Company, IPR2017-01120, U.S. Pat. No. 8,899,239, Exhibit 1025, Excerpts from James W. Dally, Packaging of Electronic Systems: A Mechanical Engineering Approach (1990), Apr. 3, 2017.
R.J. Reynolds Vapor Company, IPR2017-01120, U.S. Pat. No. 8,899,239, Exhibit 1026, U.S. Pat. No. 5,144,962 ("Counts"), Apr. 3, 2017.
R.J. Reynolds Vapor Company, IPR2017-01120, U.S. Pat. No. 8,899,239, Exhibit 1027, U.S. Pat. No. 7,034,814 ("Gong"), Apr. 3, 2017.
R.J. Reynolds Vapor Company, IPR2017-01120, U.S. Pat. No. 8,899,239, Exhibit 1028, Declaration of James Donnelly, Apr. 3, 2017.
R.J. Reynolds Vapor Company, Petition for Inter Partes Review of U.S. Pat. No. 8,889,239—IPR2016-01272, Paper 2, Jul. 2, 2016.
R.J. Reynolds Vapor Company, Petition for Inter Partes Review of U.S. Pat. No. 8,889,239—IPR2016-01272, Ex. 1001 U.S. Pat. No. 8,899,239 ("The 239 patent"), Jul. 2, 2016.
R.J. Reynolds Vapor Company, Petition for Inter Partes Review of U.S. Pat. No. 8,889,239—IPR2016-01272, Ex. 1002 U.S. Pat. No. 3,479,561 ("The 561 patent"), Jul. 2, 2016.
R.J. Reynolds Vapor Company, Petition for Inter Partes Review of U.S. Pat. No. 8,889,239—IPR2016-01272, Ex. 1003 Japanese Unexamined Patent Application Publication No. 2001-291598 ("JP598" or "JP98 publication"), Jul. 2, 2016.
R.J. Reynolds Vapor Company, Petition for Inter Partes Review of U.S. Pat. No. 8,889,239—IPR2016-01272, Ex. 1004 Certified translation of Japanese Unexamined Patent Application Publication No. 2001-291598 ("JP598" or "JP598 publication"), Jul. 2, 2016.
R.J. Reynolds Vapor Company, Petition for Inter Partes Review of U.S. Pat. No. 8,889,239—IPR2016-01272, Ex. 1005 Japanese Unexamined Patent Application Publication No. H9-326299 ("JP299" or "JP299 publication"), Jul. 2, 2016.
R.J. Reynolds Vapor Company, Petition for Inter Partes Review of U.S. Pat. No. 8,889,239—IPR2016-01272, Ex. 1006 Certified translation of Japanese Unexamined Patent Application Publication No. H9-326299 ("JP299" or "JP299 publication"), Jul. 2, 2016.
R.J. Reynolds Vapor Company, Petition for Inter Partes Review of U.S. Pat. No. 8,889,239—IPR2016-01272, Ex. 1007 Excerpts from 239 Patent File History, Jul. 2, 2016.
R.J. Reynolds Vapor Company, Petition for Inter Partes Review of U.S. Pat. No. 8,889,239—IPR2016-01272, Ex. 1008 Plaintiff's Responsive Claim Construction Brief from *Fontem Ventures, B. V. et al. v. NJOY, Inc. et al*, Case No. 14-cv-1645-GW (MRWx) (C.D. Cal. Apr. 23, 2015) (Dkt No. 117), Jul. 2, 2016.
R.J. Reynolds Vapor Company, Petition for Inter Partes Review of U.S. Pat. No. 8,889,239—IPR2016-01272, Ex. 1009 Ex. 3 attached to Plaintiff's Responsive Claim Construction Brief from *Fontem Ventures, B. V. et al. v. NJOY, Inc. et al*, Case No. 14-cv-1645-GW (MRWx) (C.D. Cal. Apr. 23, 2015) (Dkt No. 117-2), Jul. 2, 2016.
R.J. Reynolds Vapor Company, Petition for Inter Partes Review of U.S. Pat. No. 8,889,239—IPR2016-01272, Ex. 1010 Ex. 4 attached

(56) References Cited

OTHER PUBLICATIONS to Plaintiff's Responsive Claim Construction Brief from *Fontem Ventures, B. V. et al.* v. *NJOY, Inc. et al*, Case No. 14-cv-1645-GW (MRWx) (C.D. Cal. Apr. 23, 2015) (Dkt No. 117-2), Jul. 2, 2016.
R.J. Reynolds Vapor Company, Petition for Inter Partes Review of U.S. Pat. No. 8,889,239—IPR2016-01272, Ex. 1011 Ex. 5 attached to Plaintiff's Responsive Claim Construction Brief from *Fontem Ventures, B. V. et al.* v. *NJOY, Inc. et al*, Case No. 14-cv-1645-GW (MRWx) (C.D. Cal. Apr. 23, 2015) (Dkt No. 117-2), Jul. 2, 2016.
R.J. Reynolds Vapor Company, Petition for Inter Partes Review of U.S. Pat. No. 8,889,239—IPR2016-01272, Ex. 1012 Declaration of Robert H. Sturges regarding U.S. Pat. No. 8,899,239, Jul. 2, 2016.
R.J. Reynolds Vapor Company, Petition for Inter Partes Review of U.S. Pat. No. 8,889,239—IPR2016-01272, Ex. 1013 Excerpt from Mark's Standard Handbook for Mechanical Engineers (1978), Jul. 2, 2016.
R.J. Reynolds Vapor Company, Petition for Inter Partes Review of U.S. Pat. No. 8,899,239—IPR2017-01120, Apr. 3, 2017.
R.J. Reynolds Vapor Company, Power of Attorney, Inter Partes Review of U.S. Pat. No. 8,899,239—IPR2017-01120, Apr. 3, 2017.
R.J. Reynolds Vapor Company, Preliminary Invalidity Contentions served in *Fontem Ventures B.V.* v. *R.J. Reynolds Vapor Company*, U.S. District Court for the Middle District of North Carolina, 16-cv-01255, Mar. 15, 2017.
R.J. Reynolds Vapor Company, Preliminary Invalidity Contentions, Exhibit D ('239 patent), 16-cv-01255, Mar. 15, 2017.
State Intellectual Property Office, China, "International Search Report for PCT/CN2004/000182", dated Jun. 10, 2004, 2 pages.
State Intellectual Property Office, China, "Examination Decision on the Request for Invalidation for CN03212882.7", dated Dec. 25, 2007.
Taiwan Patent Office, "English Translation of Official Letter including Search Report for Taiwanese Patent Application No. 093111573", dated Apr. 24, 2009, 3 pages.
U.S. District Court, Central District of California , Western Division, Defendant NJOY, Inc.'s Exhibit 1 to Defendants' Motion for Leave to Amend Invalidity Contentions dated Jun. 29, 2015 and filed in Consolidated Case No. CV 14-01645 GW (MRW) and related consolidated cases.
U.S. District Court, Central District of California , Western Division, Defendant NJOY, Inc.'s Exhibit 2 to Defendants' Motion for Leave to Amend Invalidity Contentions dated Jun. 29, 2015 and filed in Consolidated Case No. CV 14-01645 GW (MRW) and related consolidated cases.
U.S. District Court, Central District of California ,Western Division, Defendant NJOY, Inc.'s Exhibit 3 to Defendants' Motion for Leave to Amend Invalidity Contentions dated 06/29/201 and filed in Consolidated Case No. CV 14-01645 GW (MRW) and related consolidated cases.
U.S. District Court, Central District of California ,Western Division, Defendant NJOY, Inc.'s production documents VLACHOS 0000061-72; Consolidated Case No. CV 14-01645 GW (MRW) and related consolidated cases.
U.S. District Court, Central District of California ,Western Division, Defendant NJOY, Inc.'s production documents VLACHOS 0000061-72; Jun. 29, 2015 in Consolidated Case No. CV 14-01645 GW (MRW) and related consolidated cases.
U.S. District Court, Central District of California, Wester N Division, Defendant NJOY, Inc.'s Reply Brief in Support of Defendants' Motion for Leave to Amend Invalidity Contentions dated Jul. 13, 2015 and filed in Consolidated Case No. CV 14-01645 GW (MRW) and related consolidated cases.
U.S. District Court, Central District of California, Western Division, Defendant NJOY, Inc.'s Memorandum of Points and Authorities in Support of Defendants' Motion for Leave to Amend Invalidity Contentions dated Jun. 29, 2015 and filed in Consolidated Case No. CV 14-01645 GW (MRW) and related consolidated cases.
U.S. District Court, Central District of California, Western Division, Defendant NJOY, Inc.'s Declaration of Brent K. Yamashita in Support of Defendants' Motion for Leave to Amend Invalidity Contentions dated Jun. 29, 2015 and filed in Consolidated Case No. CV 14-01645 GW (MRW) and related consolidated cases.
U.S. District Court, Central District of California, Western Division, Defendant NJOY, Inc.'s Exhibit 4 to Defendants' Motion for Leave to Amend Invalidity Contentions dated Jun. 29, 2015 and filed in Consolidated Case No. CV 14-01645 GW (MRW) and related consolidated cases.
U.S. District Court, Central District of California, Western Division, Defendant NJOY, Inc.'s Exhibit 5 to Defendants' Motion for Leave to Amend Invalidity Contentions dated Jun. 29, 2015 and filed in Consolidated Case No. CV 14-01645 GW (MRW) and related consolidated cases.
Ukraine Patent Office, "English Translation of Examination Report for Ukrainian Patent Application No. 200511258", dated Feb. 4, 2009, 2 pages.
United States Patent and Trademark Office, "Final Office Action for U.S. Appl. No. 13/921,582", dated Aug. 28, 2014, 9 pages.
United States Patent and Trademark Office, "Non-Final Office Action for U.S. Appl. No. 10/547,244", dated Nov. 12, 2009, 7 pages.
United States Patent and Trademark Office, "Non-Final Office Action for U.S. Appl. No. 10/547,244", dated Jul. 21, 2010, 7 pages.
United States Patent and Trademark Office, "Non-Final Office Action for U.S. Appl. No. 10/547,244", dated Jul. 26, 2011, 10 pages.
United States Patent and Trademark Office, "Non-Final Office Action for U.S. Appl. No. 13/088,276", dated May 21, 2012, 8 pages.
United States Patent and Trademark Office, "Non-Final Office Action for U.S. Appl. No. 13/548,659", dated Mar. 15, 2013, 8 pages.
United States Patent and Trademark Office, "Non-Final Office Action for U.S. Appl. No. 13/921,582", dated Mar. 20, 2014, 7 pages.
United States Patent and Trademark Office, "Notice of Allowance for U.S. Appl. No. 13/088,276", dated Apr. 15, 2013, 8 pages.
United States Patent and Trademark Office, "Notice of Allowance for U.S. Appl. No. 14/289,366", dated Sep. 11, 2014, 12 pages.
United States Patent and Trademark Office, Final Office Action for U.S. Appl. No. 14/328,561, dated Jun. 1, 2015, 6 pages.
United States Patent and Trademark Office, Final Office Action for U.S. Appl. No. 15/091,296, dated Dec. 16, 2016, 7 pgs.
United States Patent and Trademark Office, Non-Final Office Action for U.S. Appl. No. 14/328,561, dated Jan. 29, 2015, 6 pages.
United States Patent and Trademark Office, Non-Final Office Action for U.S. Appl. No. 14/328,561, dated Sep. 24, 2015, 12 pages.
United States Patent and Trademark Office, Patent Trial and Appeal Board, IPR2016-01272, Paper 11, Decision Instituting Inter Partes Review, Dec. 30, 2016.
R.J. Reynolds Vapor Company, Preliminary Invalidity Contentions for 17-cv-0175, Jul. 31, 2017.
R.J. Reynolds Vapor Company, Preliminary Invalidity Contentions, Exhibit G (U.S. Pat. No. 9,364,027), 17-cv-0175, Jul. 31, 2017.
USPTO, Non-Final Office Action for U.S. Appl. No. 15/169,929, dated Dec. 6, 2016.
Patent Trial and Appeal Board, USPTO, Decision—Instituting Inter Partes Review, *R.J. Reynolds Vapor Company* v. *Fontem Holdings 1 B.V.*, IPR2017-01120, Paper 11, Oct. 23, 2017.
R.J. Reynolds Vapor Company, Motion for Leave to Amend Preliminary Invalidity Contentions and Elections, *Fontem Ventures et al.* v. *R.J. Reynolds Vapor Company*, 1:16-cv-01255 and consolidated cases, U.S. District Court for the Middle District of North Carolina, Dkt. 111, Oct. 23, 2017.
R.J. Reynolds Vapor Company, Brief in Support of Motion for Leave to Amend Preliminary Invalidity Contentions and Elections, *Fontem Ventures et al.* v. *R.J. Reynolds Vapor Company*, 1:16-cv-01255 and consolidated cases, U.S. District Court for the Middle District of North Carolina, Dkt. 112, Oct. 23, 2017.
R.J. Reynolds Vapor Company, Declaration of Robert Mallin in Support of Motion for Leave to Amend Preliminary Invalidity Contentions and Elections, *Fontem Ventures et al.* v. *R.J. Reynolds*

(56) References Cited

OTHER PUBLICATIONS

*Vapor Company*, 1:16-cv-01255 and consolidated cases, U.S. District Court for the Middle District of North Carolina, Dkt. 113, Oct. 23, 2017.
R.J. Reynolds Vapor Company, Exhibits 1-24 to Declaration of Robert Mallin in Support of Motion for Leave to Amend Preliminary Invalidity Contentions and Elections, *Fontem Ventures et al.* v. *R.J. Reynolds Vapor Company*, 1:16-cv-01255 and consolidated cases, U.S. District Court for the Middle District of North Carolina, Dkt. 113-1 through 113-24, Oct. 23, 2017.
Patent Trial and Appeal Board, USPTO, Final Written Decision, *R.J. Reynolds Vapor Company* v. *Fontem Holdings 1 B.V.*, IPR2016-01272, Paper 51, Dec. 21, 2017.
R.J. Reynolds Vapor Company, Amended Preliminary Invalidity Contentions (for U.S. Pat. Nos. 8,365,742, 8,490,628, 8,893,726, 8,899,239, 9,326,548, 9,326,549, and 9,370,205, served in *Fontem Ventures B.V.* v. *R.J. Reynolds Vapor Company*, U.S. District Court for the Middle District of North Carolina, 16-cv-01255 and consolidated cases, Oct. 13, 2017.
R.J. Reynolds Vapor Company, Amended Preliminary Invalidity Contentions, Amended Exhibit D (U.S. Pat. No. 8,899,239), served in *Fontem Ventures B.V.* v. *R.J. Reynolds Vapor Company*, U.S. District Court for the Middle District of North Carolina, 16-cv-01255 and consolidated cases, Oct. 13, 2017.
R.J. Reynolds Vapor Company, Amended Preliminary Invalidity Contentions (for U.S. Pat. Nos. 8,375,957, 8,863,752, 9,326,550, 9,326,551, 9,339,062, 8,393,331, 9,364,027, and 9,456,632, served in *Fontem Ventures B.V.* v. *R.J. Reynolds Vapor Company*, U.S. District Court for the Middle District of North Carolina, 16-cv-01255 and consolidated cases, Oct. 13, 2017.
R.J. Reynolds Vapor Company, Amended Preliminary Invalidity Contentions, Amended Exhibit G (U.S. Pat. No. 9,364,027), served in *Fontem Ventures B.V.* v. *R.J. Reynolds Vapor Company*, U.S. District Court for the Middle District of North Carolina, 16-cv-01255 and consolidated cases, Oct. 13, 2017.
R.J. Reynolds Vapor Company, Petition for Inter Partes Review of U.S. Pat. No. 9,364,027—IPR2018-00629, Mar. 2, 2018.
R.J.Reynolds Vapor Company, IPR2018-00629, Ex. 1001—U.S. Pat. No. 9,364,027 ("The '027 the Patent"), Mar. 2, 2018.
R.J. Reynolds Vapor Company, IPR2018-00629, Ex. 1002—Declaration of Dr. Robert H. Sturges regarding U.S. Pat. No. 9,364,027, Mar. 2, 2018.
R.J. Reynolds Vapor Company, IPR2018-00629, Ex. 1003—Chinese Patent Application Publication No. CN1233436A, Mar. 2, 2018.
R.J. Reynolds Vapor Company, IPR2018-00629, Ex. 1004—Certified translation of Chinese Patent Application Publication No. CN1233436A ("Hongbin"), Mar. 2, 2018.
R.J.Reynolds Vapor Company, IPR2018-00629, Ex. 1005—U.S. Pat. No. 3,479,561 ("Janning"), Mar. 2, 2018.
R.J. Reynolds Vapor Company, IPR2018-00629, Ex. 1006—Japanese Unexamined Patent Application Publication No. 2001-291598, Mar. 2, 2018.
R.J. Reynolds Vapor Company, IPR2018-00629, Ex. 1007—Certified translation of Japanese Unexamined Patent Application Publication No. 2001-291598 ("JP598" or "JP598 publication"), Mar. 2, 2018.
R.J. Reynolds Vapor Company, IPR2018-00629, Ex. 1008—U.S. Pat. No. 5,060,671 ("Counts '671"), Mar. 2, 2018.
R.J. Reynolds Vapor Company, IPR2018-00629, Ex. 1009—Korean Patent Application Publication No. 2002-0067473, Mar. 2, 2018.
R.J. Reynolds Vapor Company, IPR2018-00629, Ex. 1010—Certified translation of Korean Patent Application Publication No. 2002-0067473 ("KR473"), Mar. 2, 2018.
R.J. Reynolds Vapor Company, IPR2018-00629, Ex. 1011—U.S. Pat. No. 6,155,268 ("Takeuchi"), Mar. 2, 2018.
R.J. Reynolds Vapor Company, IPR2018-00629, Ex. 1012—Final Written Decision of Inter Partes Review dated Dec. 21, 2017 (Paper 51), *R.J. Reynolds Vapor Company* v. *Fontem Holdings 1 B.V.*, IPR2016-01272 (P.T.A.B., petition filed Jul. 2, 2016) ("IPR2016-01272 FWD"), Mar. 2, 2018.
R.J. Reynolds Vapor Company, IPR2018-00629, Ex. 1013—Institution Decision of Inter Partes Review dated Dec. 30, 2016 (Paper 11), *R.J. Reynolds Vapor Company* v. *Fontem Holdings 1 B.V.*, IPR2016-01272 (P.T.A.B., petition filed Jul. 2, 2016) ("IPR2016-01272 Institution Decision"), Mar. 2, 2018.
R.J. Reynolds Vapor Company, IPR2018-00629, Ex. 1014—Institution Decision of Inter Partes Review dated Oct. 23, 2017 (Paper 11), *R.J. Reynolds Vapor Company* v. *Fontem Holdings 1 B.V.*, IPR2017-01120 (P.T.A.B., petition filed Apr. 4, 2017) ("IPR2017-01120 Institution Decision"), Mar. 2, 2018.
R.J. Reynolds Vapor Company, IPR2018-00629, Ex. 1015—Plaintiff's Responsive Claim Construction Brief from *Fontem Ventures, B. V. et al.* v. *NJOY, Inc. et al*, Case No. 14-cv-1645-GW (MRWx) (C.D. Cal. Apr. 23, 2015) (Dkt No. 117) ("PO Claim Construction Brief in NJOY Litigation"), Mar. 2, 2018.
R.J. Reynolds Vapor Company, IPR2018-00629, Ex. 1016—Ex. 3 attached to Plaintiff's Responsive Claim Construction Brief from *Fontem Ventures, B. V. et al.* v. *NJOY, Inc. et al*, Case No. 14-cv-1645-GW (MRWx) (C.D. Cal. Apr. 23, 2015) (Dkt No. 117-2), Mar. 2, 2018.
R.J. Reynolds Vapor Company, IPR2018-00629, Ex. 1017—Ex. 4 attached to Plaintiff's Responsive Claim Construction Brief from *Fontem Ventures, B. V. et al.* v. *NJOY, Inc. et al*, Case No. 14-cv-1645-GW (MRWx) (C.D. Cal. Apr. 23, 2015) (Dkt No. 117-2), Mar. 2, 2018.
R.J. Reynolds Vapor Company, IPR2018-00629, Ex. 1018—Ex. 5 attached to Plaintiff's Responsive Claim Construction Brief from *Fontem Ventures, B. V. et al.* v. *Njoy, Inc. et al*, Case No. 14-cv-1645-GW (MRWx) (C.D. Cal. Apr. 23, 2015) (Dkt No. 117-2), Mar. 2, 2018.
R.J. Reynolds Vapor Company, IPR2018-00629, Ex. 1019—Mosdesign Semiconductor Corp. Datasheet for M1600 LED Drivers ("Mosdesign M1600 Datasheet"), Mar. 2, 2018.
R.J. Reynolds Vapor Company, IPR2018-00629, Ex. 1020—Merriam-Webster's Collegiate Dictionary, Tenth Edition, Merriam-Webster, Inc. 2002—Excerpt, Mar. 2, 2018.
R.J. Reynolds Vapor Company, IPR2018-00629, Ex. 1021—Dr. Sturges Deposition Transcript, *R.J. Reynolds Vapor Company* v. *Fontem Holdings 1 B.V.*, IPR2016-01272, Exhibit 2020 (PTAB Mar. 29, 2017) (petition filed Jul. 2, 2016) ("IPR2016-01272 Dr. Sturges Deposition"), Mar. 2, 2018.
R.J. Reynolds Vapor Company, IPR2018-00629, Ex. 1022—Dr. Sturges Reply Deposition Transcript, *R.J. Reynolds Vapor Company* v. *Fontem Holdings 1 B.V.*, IPR2016-01272, Exhibit 2023 (PTAB Aug. 4, 2017) (petition filed Jul. 2, 2016) ("IPR2016-01272 Dr. Sturges Reply Deposition"), Mar. 2, 2018.
R.J. Reynolds Vapor Company, IPR2018-00629, Ex. 1024—Dr. Schaafsma Deposition Transcript, *R.J. Reynolds Vapor Company* v. *Fontem Holdings 1 B.V.*, IPR2016-01272, Exhibit 1016 (PTAB Jun. 23, 2017) (petition filed Jul. 2, 2016) ("IPR2016-01272 Dr. Schaafsma Deposition"), Mar. 2, 2018.
R.J. Reynolds Vapor Company, IPR2018-00629, Ex. 1025—U.S. Pat. No. 5,144,962 ("Counts"), Mar. 2, 2018.
R.J. Reynolds Vapor Company, IPR2018-00629, Ex. 1026—U.S. Pat. No. 2,057,353 ("Whittemore"), Mar. 2, 2018.
R.J. Reynolds Vapor Company, IPR2018-00629, Ex. 1027—U.S. Pat. No. 6,598,607 ("Adiga"), Mar. 2, 2018.
R.J. Reynolds Vapor Company, IPR2018-00629, Ex. 1028—U.S. Pat. No. 4,793,365 ("Sensabaugh"), Mar. 2, 2018.
R.J. Reynolds Vapor Company, IPR2018-00629, Ex. 1029—U.S. Pat. No. 5,203,355 ("Clearman"), Mar. 2, 2018.
R.J. Reynolds Vapor Company, IPR2018-00629, Ex. 1030—U.S. Pat. No. 2,472,282 ("Burchett"), Mar. 2, 2018.
R.J. Reynolds Vapor Company, IPR2018-00629, Ex. 1031—U.S. Pat. No. 2,032,695 ("Gimera"), Mar. 2, 2018.
R.J. Reynolds Vapor Company, IPR2018-00629, Ex. 1032—European Publication No. EP0845220A1 ("Susa"), Mar. 2, 2018.
R.J. Reynolds Vapor Company, IPR2018-00629, Ex. 1033—The Oxford Modern English Dictionary, Second Edition, Oxford University Press, 1996—Excerpt, Mar. 2, 2018.

(56) References Cited

OTHER PUBLICATIONS

R.J. Reynolds Vapor Company, IPR2018-00629, Ex. 1034—Marks' Standard Handbook for Mechanical Engineers, Ninth Edition, McGraw-Hill, Inc. 1978—Except, Mar. 2, 2018.
R.J. Reynolds Vapor Company, IPR2018-00629, Ex. 1035—McGraw-Hill Dictionary of Scientific and Technical Terms, Fifth Edition, McGraw-Hill, Inc. 1994—Excerpt, Mar. 2, 2018.
R.J. Reynolds Vapor Company, IPR2018-00629, Ex. 1036—U.S. Pat. No. 4,947,874 ("Brooks"), Mar. 2, 2018.
R.J. Reynolds Vapor Company, IPR2018-00629, Ex. 1037—European Publication No. EP1584910A1 ("Tohyama"), Mar. 2, 2018.
R.J.Reynolds Vapor Company, IPR2018-00629, Ex. 1038—U.S. Pat. No. 2,461,664 ("Smith"), Mar. 2, 2018.
R.J. Reynolds Vapor Company, IPR2018-00629, Ex. 1040—Richard Meyst Deposition Transcript, *R.J. Reynolds Vapor Company* v. *Fontem Holdings 1 B.V.*, IPR2016-01272, Exhibit 1015 (PTAB Jun. 23, 2017) (petition filed Jul. 2, 2016) ("IPR2016-01272 Meyst Deposition"), Mar. 2, 2018.
R.J. Reynolds Vapor Company, IPR2018-00629, Ex. 1041—Declaration of Joshua P. Smith, Mar. 2, 2018.
R.J. Reynolds Vapor Company, Petition for Inter Partes Review of U.S. Pat. No. 9,364,027—IPR2018-00630, Mar. 2, 2018.
R.J. Reynolds Vapor Company, IPR2018-00630, Ex. 1001—U.S. Pat. No. 9,364,027 ("The '027 Patent"), Mar. 2, 2018.
R.J. Reynolds Vapor Company, IPR2018-00630, Ex. 1002—Declaration of Dr. Robert H. Sturges regarding U.S. Pat. No. 9,364,027, Mar. 2, 2018.
R.J. Reynolds Vapor Company, IPR2018-00630, Ex. 1003—Chinese Patent Application Publication No. CN1233436A, Mar. 2, 2018.
R.J. Reynolds Vapor Company, IPR2018-00630, Ex. 1004—Certified translation of Chinese Patent Application Publication No. CN1233436A ("Hongbin"), Mar. 2, 2018.
R.J. Reynolds Vapor Company, IPR2018-00630, Ex. 1005—U.S. Pat. No. 3,479,561 ("Janning"), Mar. 2, 2018.
R.J. Reynolds Vapor Company, IPR2018-00630, Ex. 1006—Japanese Unexamined Patent Application Publication No. 2001-291598, Mar. 2, 2018.
R.J. Reynolds Vapor Company, IPR2018-00630, Ex. 1007—Certified translation of Japanese Unexamined Patent Application Publication No. 2001-291598 ("JP598" or "JP598 publication"), Mar. 2, 2018.
R.J. Reynolds Vapor Company, IPR2018-00630, Ex. 1009—Korean Patent Application Publication No. 2002-0067473, Mar. 2, 2018.
R.J. Reynolds Vapor Company, IPR2018-00630, Ex. 1010—Certified translation of Korean Patent Application Publication No. 2002-0067473 ("KR473"), Mar. 2, 2018.
R.J. Reynolds Vapor Company, IPR2018-00630, Ex. 1012—Final Written Decision of Inter Partes Review dated Dec. 21, 2017 (Paper 51), *R.J. Reynolds Vapor Company* v. *Fontem Holdings 1 B.V.*, IPR2016-01272 (P.T.A.B., petition filed Jul. 2, 2016) ("IPR2016-01272 FWD"), Mar. 2, 2018.
R.J. Reynolds Vapor Company, IPR2018-00630, Ex. 1013—Institution Decision of Inter Partes Review dated Dec. 30, 2016 (Paper 11), *R.J. Reynolds Vapor Company* v. *Fontem Holdings 1 B.V.*, IPR2016-01272 (P.T.A.B., petition filed Jul. 2, 2016) ("IPR2016-01272 Institution Decision"), Mar. 2, 2018.
R.J. Reynolds Vapor Company, IPR2018-00630, Ex. 1014—Institution Decision of Inter Partes Review dated Oct. 23, 2017 (Paper 11), *R.J. Reynolds Vapor Company* v. *Fontem Holdings 1 B.V.*, IPR2017-01120 (P.T.A.B., petition filed Apr. 4, 2017) ("IPR2017-01120 Institution Decision"), Mar. 2, 2018.
R.J. Reynolds Vapor Company, IPR2018-00630, Ex. 1015—Plaintiff's Responsive Claim Construction Brief from *Fontem Ventures, B. V. et al.* v. *NJOY, Inc. et al*, Case No. 14-cv-1645-GW (MRWx) (C.D. Cal. Apr. 23, 2015) (Dkt No. 117) ("PO Claim Construction Brief in NJOY Litigation"), Mar. 2, 2018.
R.J. Reynolds Vapor Company, IPR2018-00630, Ex. 1016—Ex. 3 attached to Plaintiff's Responsive Claim Construction Brief from *Fontem Ventures, B. V. et al.* v. *NJOY, Inc. et al*, Case No. 14-cv-1645-GW (MRWx) (C.D. Cal. Apr. 23, 2015) (Dkt No. 117-2), Mar. 2, 2018.
R.J. Reynolds Vapor Company, IPR2018-00630, Ex. 1017—Ex. 4 attached to Plaintiff's Responsive Claim Construction Brief from *Fontem Ventures, B. V. et al.* v. *NJOY, Inc. et al*, Case No. 14-cv-1645-GW (MRWx) (C.D. Cal. Apr. 23, 2015) (Dkt No. 117-2), Mar. 2, 2018.
R.J. Reynolds Vapor Company, IPR2018-00630, Ex. 1018—Ex. 5 attached to Plaintiff's Responsive Claim Construction Brief from *Fontem Ventures, B. V. et al.* v. *NJOY, Inc. et al*, Case No. 14-cv-1645-GW (MRWx) (C.D. Cal. Apr. 23, 2015) (Dkt No. 117-2), Mar. 2, 2018.
R.J. Reynolds Vapor Company, IPR2018-00630, Ex. 1019—Mosdesign Semiconductor Corp. Datasheet for M1600 LED Drivers ("Mosdesign M1600 Datasheet"), Mar. 2, 2018.
R.J. Reynolds Vapor Company, IPR2018-00630, Ex. 1020—Merriam-Webster's Collegiate Dictionary, Tenth Edition, Merriam-Webster, Inc. 2002—Excerpt, Mar. 2, 2018.
R.J. Reynolds Vapor Company, IPR2018-00630, Ex. 1021—Dr. Sturges Deposition Transcript, *R.J. Reynolds Vapor Company* v. *Fontem Holdings 1 B.V.*, IPR2016-01272, Exhibit 2020 (PTAB Mar. 29, 2017) (petition filed Jul. 2, 2016) ("IPR2016-01272 Dr. Sturges Deposition"), Mar. 2, 2018.
R.J. Reynolds Vapor Company, IPR2018-00630, Ex. 1022—Dr. Sturges Reply Deposition Transcript, *R.J. Reynolds Vapor Company* v. *Fontem Holdings 1 B.V.*, IPR2016-01272, Exhibit 2023 (PTAB Aug. 4, 2017) (petition filed Jul. 2, 2016) ("IPR2016-01272 Dr. Sturges Reply Deposition"), Mar. 2, 2018.
R.J. Reynolds Vapor Company, IPR2018-00630, Ex. 1024—Dr. Schaafsma Deposition Transcript, *R.J. Reynolds Vapor Company* v. *Fontem Holdings 1 B.V.*, IPR2016-01272, Exhibit 1016 (PTAB Jun. 23, 2017) (petition filed Jul. 2, 2016) ("IPR2016-01272 Dr. Schaafsma Deposition"), Mar. 2, 2018.
R.J. Reynolds Vapor Company, IPR2018-00630, Ex. 1025—U.S. Pat. No. 5,144,962 ("Counts"), Mar. 2, 2018.
R.J. Reynolds Vapor Company, IPR2018-00630, Ex. 1026—U.S. Pat. No. 2,057,353 ("Whittemore"), Mar. 2, 2018.
R.J. Reynolds Vapor Company, IPR2018-00630, Ex. 1027—U.S. Pat. No. 5,144,962 ("Counts").
R.J. Reynolds Vapor Company, IPR2018-00630, Ex. 1028—U.S. Pat. No. 2,959,664 ("Fenn").
R.J. Reynolds Vapor Company, IPR2018-00630, Ex. 1029—U.S. Pat. No. 2,269,394 ("Cuno").
R.J. Reynolds Vapor Company, IPR2018-00630, Ex. 1030—U.S. Pat. No. 2,104,266 ("McCormick").
R.J. Reynolds Vapor Company, IPR2018-00630, Ex. 1033—The Oxford Modern English Dictionary, Second Edition, Oxford University Press, 1996—Excerpt, Mar. 2, 2018.
R.J. Reynolds Vapor Company, IPR2018-00630, Ex. 1035—McGraw-Hill Dictionary of Scientific and Technical Terms, Fifth Edition, McGraw-Hill, Inc. 1994—Excerpt, Mar. 2, 2018.
R.J. Reynolds Vapor Company, IPR2018-00630, Ex. 1036—Richard Meyst Deposition Transcript, *R.J. Reynolds Vapor Company* v. *Fontem Holdings 1 B.V.*, IPR2016-01272, Exhibit 1015 (PTAB Jun. 23, 2017) (petition filed Jul. 2, 2016) ("IPR2016-01272 Meyst Deposition"), Mar. 2, 2018.
R.J. Reynolds Vapor Company, IPR2018-00630, Ex. 1037—Declaration of Joshua P. Smith, Mar. 2, 2018.
Case 1:16-cv-01255-CCE-JEP, Dkt. No. 148., *Fontem Ventures B.V. and Fontem Holdings 1 B.V.* v. *R.J. Reynolds Vapor Company*, Claim Construction Order, Mar. 12, 2018, 8 pages.
Case 2:14-cv-01645-GW-MRW, Dkt. No. 65, *Fontem Ventures B.V. et al.* v. *NJOY, Inc. et al.* Court's Rulings on Claims Construction, Jan. 29, 2015, 28 pages.
Case No. CV 14/1645-GW(MRWx), Dkt. No. 133, *Fontem Ventures B.V. et al.* v. *NJOY, Inc. et al.* Order regarding Markman Hearing/ Claim Construction, May 7, 2015, 16 pages.
R.J. Reynolds Vapor Company, *R.J. Reynolds Vapor Company* v. *Fontem Holdings 1 B.V.*, IPR2017-01120, Paper 9—Petitioner Reply to Patent Owner Preliminary Response, Sep. 7, 2017, filed with exhibits 1029-1030 below.

(56) References Cited

OTHER PUBLICATIONS

R.J. Reynolds Vapor Company, *R.J. Reynolds Vapor Company v. Fontem Holdings 1 B.V.*, IPR2017-01120, Paper 28—Petitioner Reply to Patent Owner Opposition, Apr. 10, 2018, filed with exhibits 1031-1062 below.

R.J. Reynolds Vapor Company, *R.J. Reynolds Vapor Company v. Fontem Holdings 1 B.V.*, IPR2017-01120, Ex. 1029, Declaration of R. Mallin, Sep. 7, 2017.

R.J. Reynolds Vapor Company, *R.J. Reynolds Vapor Company v. Fontem Holdings 1 B.V.*, IPR2017-01120, Ex. 1030, Jan. 9, 2017 Fontem Infringement Contentions, Sep. 7, 2017.

R.J. Reynolds Vapor Company, *R.J. Reynolds Vapor Company v. Fontem Holdings 1 B.V.*, IPR2017-01120, Ex. 1031, Annotated Fig. 3 of JP598 from Deposition of David Schaafsma, Mar. 15, 2018, Apr. 10, 2018.

R.J. Reynolds Vapor Company, *R.J. Reynolds Vapor Company v. Fontem Holdings 1 B.V.*, IPR2017-01120, Ex. 1032, Deposition Transcript of David Schaafsma, Jun. 8, 2017, in IPR2016-01272, Apr. 10, 2018.

R.J. Reynolds Vapor Company, *R.J. Reynolds Vapor Company v. Fontem Holdings 1 B.V.*, IPR2017-01120, Ex. 1033, Deposition Transcript of Richard Meyst, Jun. 6, 2017, in 1PR2016-01272, Apr. 10, 2018.

R.J. Reynolds Vapor Company, *R.J. Reynolds Vapor Company v. Fontem Holdings 1 B.V.*, IPR2017-01120, Ex. 1034, Deposition Transcript of Richard Meyst, Mar. 20, 2018, Apr. 10, 2018.

R.J. Reynolds Vapor Company, *R.J. Reynolds Vapor Company v. Fontem Holdings 1 B.V.*, IPR2017-01120, Ex. 1035, Deposition Transcript of David Schaafsma, Mar. 15, 2018, Apr. 10, 2018.

R.J. Reynolds Vapor Company, *R.J. Reynolds Vapor Company v. Fontem Holdings 1 B.V.*, IPR2017-01120, Ex. 1036, Reply Declaration of Dr. Robert H. Sturges regarding U.S. Pat. No. 8,899,239, Apr. 10, 2018.

R.J. Reynolds Vapor Company, *R.J. Reynolds Vapor Company v. Fontem Holdings 1 B.V.*, IPR2017-01120, Ex. 1037, Excerpt from the Oxford Modern English Dictionary, 2nd ed. (1996), Apr. 10, 2018.

R.J. Reynolds Vapor Company, *R.J. Reynolds Vapor Company v. Fontem Holdings 1 B.V.*, IPR2017-01120, Ex. 1038, Excerpt from Concise Oxford English Dictionary, 10th ed. (2002), Apr. 10, 2018.

R.J. Reynolds Vapor Company, *R.J. Reynolds Vapor Company v. Fontem Holdings 1 B.V.*, IPR2017-01120, Ex. 1039, Excerpt from Merriam-Webster Dictionary Home and Office Edition (1998), Apr. 10, 2018.

R.J. Reynolds Vapor Company, *R.J. Reynolds Vapor Company v. Fontem Holdings 1 B.V.*, IPR2017-01120, Ex. 1040, Excerpt from Webster's New American Dictionary (1995), Apr. 10, 2018.

R.J. Reynolds Vapor Company, *R.J. Reynolds Vapor Company v. Fontem Holdings 1 B.V.*, IPR2017-01120, Ex. 1041, Excerpt from American Heritage College Dictionary, 3rd ed. (1997), Apr. 10, 2018.

R.J. Reynolds Vapor Company, *R.J. Reynolds Vapor Company v. Fontem Holdings 1 B.V.*, IPR2017-01120, Ex. 1042, U.S. Pat. No. 5,060,671 ("Counts '671"), Apr. 10, 2018.

R.J. Reynolds Vapor Company, *R.J. Reynolds Vapor Company v. Fontem Holdings 1 B.V.*, IPR2017-01120, Ex. 1043, European Publication No. EP0845220 ("Susa"), Apr. 10, 2018.

R.J. Reynolds Vapor Company, *R.J. Reynolds Vapor Company v. Fontem Holdings 1 B.V.*, IPR2017-01120, Ex. 1044, U.S. Pat. No. 3,992,598 ("Welsh"), Apr. 10, 2018.

R.J. Reynolds Vapor Company, *R.J. Reynolds Vapor Company v. Fontem Holdings 1 B.V.*, IPR2017-01120, Ex. 1045, U.S. Pat. No. 2,916,576 ("Croskey"), Apr. 10, 2018.

R.J. Reynolds Vapor Company, *R.J. Reynolds Vapor Company v. Fontem Holdings 1 B.V.*, IPR2017-01120, Ex. 1046, U.S. Pat. No. 4,437,614 ("Garcowski"), Apr. 10, 2018.

R.J. Reynolds Vapor Company, *R.J. Reynolds Vapor Company v. Fontem Holdings 1 B.V.*, IPR2017-01120, Ex. 1047, U.S. Publication No. 2012/0111347 ("Hon"), Apr. 10, 2018.

R.J. Reynolds Vapor Company, *R.J. Reynolds Vapor Company v. Fontem Holdings 1 B.V.*, IPR2017-01120, Ex. 1048, U.S. Pat. No. 1,756,053 ("Colton"), Apr. 10, 2018.

R.J. Reynolds Vapor Company, *R.J. Reynolds Vapor Company v. Fontem Holdings 1 B.V.*, IPR2017-01120, Ex. 1049, U.S. Pat. No. 2,775,006 ("Kranc"), Apr. 10, 2018.

R.J. Reynolds Vapor Company, *R.J. Reynolds Vapor Company v. Fontem Holdings 1 B.V.*, IPR2017-01120, Ex. 1050, U.S. Publication No. 2002/0181946 ("Brown"), Apr. 10, 2018.

R.J. Reynolds Vapor Company, *R.J. Reynolds Vapor Company v. Fontem Holdings 1 B.V.*, IPR2017-01120, Ex. 1051, U.S. Publication No. 2003/0170014 ("Triplett"), Apr. 10, 2018.

R.J. Reynolds Vapor Company, *R.J. Reynolds Vapor Company v. Fontem Holdings 1 B.V.*, IPR2017-01120, Ex. 1052, U.S. Pat. No. 6,236,807 ("Ruffolo"), Apr. 10, 2018.

R.J. Reynolds Vapor Company, *R.J. Reynolds Vapor Company v. Fontem Holdings 1 B.V.*, IPR2017-01120, Ex. 1053, U.S. Pat. No. 6,465,986 ("Haba"), Apr. 10, 2018.

R.J. Reynolds Vapor Company, *R.J. Reynolds Vapor Company v. Fontem Holdings 1 B.V.*, IPR2017-01120, Ex. 1054, Intelligent Systems Division, https://www.nist.g, 4/10/2018ov/el/intelligent-systems-division-73500 (last visited Apr. 6, 2018), Apr. 10, 2018.

R.J. Reynolds Vapor Company, *R.J. Reynolds Vapor Company v. Fontem Holdings 1 B.V.*, IPR2017-01120, Ex. 1055, Excerpt from Merriam-Webster's Collegiate Dictionary, 11th ed. (2003), Apr. 10, 2018.

R.J. Reynolds Vapor Company, *R.J. Reynolds Vapor Company v. Fontem Holdings 1 B.V.*, IPR2017-01120, Ex. 1056, U.S. Pat. No. 4,246,913 ("Ogden"), Apr. 10, 2018.

R.J. Reynolds Vapor Company, *R.J. Reynolds Vapor Company v. Fontem Holdings 1 B.V.*, IPR2017-01120, Ex. 1057, Deposition Transcript of Robert H. Sturges on Reply, Jul. 19, 2017, in IPR2016-012722, Apr. 10, 2018.

R.J. Reynolds Vapor Company, *R.J. Reynolds Vapor Company v. Fontem Holdings 1 B.V.*, IPR2017-01120, Ex. 1058, Declaration of Joshua P. Smith, Apr. 10, 2018.

R.J. Reynolds Vapor Company, *R.J. Reynolds Vapor Company v. Fontem Holdings 1 B.V.*, IPR2017-01120, Ex. 1059, Declaration of Robert Mallin, Apr. 10, 2018.

R.J. Reynolds Vapor Company, *R.J. Reynolds Vapor Company v. Fontem Holdings 1 B.V.*, IPR2017-01120, Ex. 1060, Email Communications between Joseph Hamilton and Robert Mallin, Dec. 21, 2017, Apr. 10, 2018.

R.J. Reynolds Vapor Company, *R.J. Reynolds Vapor Company v. Fontem Holdings 1 B.V.*, IPR2017-01120, Ex. 1061, Annotated Ex.1023 from Deposition of Robert H. Sturges on Reply, Jul. 19, 2017, in IPR2016-01272, Apr. 10, 2018.

R.J. Reynolds Vapor Company, *R.J. Reynolds Vapor Company v. Fontem Holdings 1 B.V.*, IPR2017-01120, Ex. 1062, Annotated Ex.1024 from Deposition of Robert H. Sturges on Reply, Jul. 19, 2017, in IPR2016-01272, Apr. 10, 2018.

Canadian Intellectual Property Office, Application No. CA2874924, Office Action, dated Nov. 5, 2015.

Canadian Intellectual Property Office, Application No. CA2874924, Office Action, dated Jan. 8, 2018.

R.J. Reynolds Vapor Company, Final Invalidity Contentions served in *Fontem Holdings B.V. v. R.J. Reynolds Vapor Company*, U.S. District Court for the Middle District of North Carolina, Case No. 16-cv-1255 and consolidated cases (relating to U.S. Pat. No. 8,365,742, 8,490,628, 8,893,726, 8,899,239, 8,326,548, 8,326,549, and 9,370,205), May 7, 2018.

R.J. Reynolds Vapor Company, Final Invalidity Elections served in *Fontem Holdings B.V. v. R.J. Reynolds Vapor Company*, U.S. District Court for the Middle District of North Carolina, Case No. 16-cv-1255 and consolidated cases (relating to U.S. Pat. No. 8,365,742, 8,490,628, 8,893,726, 8,899,239, 8,326,548, 8,326,549, and 9,370,205), May 7, 2018.

R.J. Reynolds Vapor Company, Final Invalidity Contentions, 16-cv-1255 and consolidated cases, Amended Exhibit D (U.S. Pat. No. 8,899,239), May 7, 2018.

R.J. Reynolds Vapor Company, Final Invalidity Contentions served in *Fontem Holdings B.V. v. R.J. Reynolds Vapor Company*, U.S. District Court for the Middle District of North Carolina, Case No.

(56) References Cited

OTHER PUBLICATIONS 16-cv-1255 and consolidated cases (relating to U.S. Pat. Nos. 8,375,957, 8,863,752 9,326,550, 9,326,551, 9,339,062, 8,393,331, 9,364,027, and 9,456,632), May 7, 2018.
R.J. Reynolds Vapor Company, Final Invalidity Elections served in *Fontem Holdings B.V.* v. *R.J. Reynolds Vapor Company*, U.S. District Court for the Middle District of North Carolina, Case No. 16-cv-1255 and consolidated cases (relating to U.S. Pat. Nos. 8,375,957, 8,863,752 9,326,550, 9,326,551, 9,339,062, 8,393,331, 9,364,027, and 9,456,632), May 7, 2018.
R.J. Reynolds Vapor Company, Final Invalidity Contentions, 16-cv-1255 and consolidated cases, Amended Exhibit G (U.S. Pat. No. 9,364,027), May 7, 2018.
U.S. District Court, Central District of California, Tentative Ruling on Summary Judgment of Invalidity, *Fontem Ventures B.V.* v. *NJOY, Inc.*, Case No. CV 14/1645-GW (MRWx), Dkt. 358 Oct. 22, 2015, 18 pgs.
USPTO, U.S. Appl. No. 13/921,582, Notice of Allowance, dated Oct. 24, 2014.
USPTO, U.S. Appl. No. 14/328,561, Notice of Allowance, dated Jan. 15, 2016.
USPTO, U.S. Appl. No. 14/328,561, Notice of Allowance, dated May 12, 2016.
USPTO, U.S. Appl. No. 15/080,341, Non-Final Office Action, dated Jun. 1, 2018.
USPTO, U.S. Appl. No. 15/091,296, Non-Final Office Action, dated Jul. 21, 2016.
USPTO, U.S. Appl. No. 15/091,296, Notice of Allowance, dated Apr. 5, 2017.
USPTO, U.S. Appl. No. 15/169,929, Notice of Allowance, dated Jun. 14, 2017.
USPTO, U.S. Appl. No. 15/632,030, Notice of Allowance, dated Nov. 7, 2017.
USPTO, U.S. Appl. No. 15/632,030, Notice of Allowance, dated Jun. 18, 2018.
USPTO, U.S. Appl. No. 15/632,030, Notice of Allowance, dated Aug. 29, 2018.
USPTO, U.S. Appl. No. 15/632,030, Corrected Notice of Allowability, dated Sep. 11, 2018.
USPTO, U.S. Appl. No. 15/914,940, Non-Final Office Action, dated Aug. 28, 2018.
USPTO, U.S. Appl. No. 16/002,230, Non-Final Office Action, dated Aug. 16, 2018.
USPTO, U.S. Appl. No. 15/080,341, Final Office Action, dated Oct. 22, 2018.
U.S. Appl. No. 16/002,230, Final Office Action, dated Jan. 17, 2019.
U.S. Appl. No. 15/914,940, Final Office Action, Mar. 21, 2019.
U.S. Appl. No. 15/080,341, Notice of Allowance, Feb. 25, 2019.
U.S. Appl. No. 16/002,230, Notice of Allowance, Feb. 26, 2019.

\* cited by examiner

ELECTRONIC CIGARETTE

This Application is a Continuation of U.S. patent application Ser. No. 15/632,030, filed Jun. 23, 2017, now U.S. Pat. No. 10,123,569, which is a Continuation of U.S. patent application Ser. No. 15/091,296 filed Apr. 5, 2016, now U.S. Pat. No. 9,713,346, which is a Continuation of U.S. patent application Ser. No. 14/328,561 filed Jul. 10, 2014, now U.S. Pat. No. 9,364,027, which is a Continuation of U.S. patent application Ser. No. 13/921,582 filed Jun. 19, 2013, now U.S. Pat. No. 8,910,641, which is a Continuation of U.S. patent application Ser. No. 13/088,276 filed Apr. 15, 2011, now U.S. Pat. No. 8,511,318, which is a Division of U.S. patent application Ser. No. 10/547,244 filed Feb. 27, 2006 and now abandoned, which is the U.S. National Phase Application of International Patent Application No. PCT/CN2004/000182 filed Mar. 8, 2004, which claims priority to Chinese Patent Application No. 03111582.9 filed Apr. 29, 2003. These applications are incorporated herein by reference.

TECHNICAL FIELD

The invention relates to an electronic cigarette which contains only nicotine without tar.

BACKGROUND ART

Despite it is commonly known that "smoking is harmful to your health", the number of smokers worldwide is up to 1 billion, and the number is increasing every year. According to the statistical data from the World Health Organization, about 4.9 million people die of diseases caused by smoking each year. Although smoking may cause serious respiratory diseases and cancer, it remains extremely difficult for smokers to quit smoking completely.

The active ingredient in a cigarette is nicotine. During smoking, nicotine, along with tar aerosol droplets produced in the burning cigarette, enters smoker's alveolus and is rapidly absorbed. After being absorbed into the blood of a smoker, nicotine then produces an effect on the receptors of the smoker's central nervous system.

Nicotine is a kind of alkaloid with low molecular weight. A small dose of nicotine is essentially harmless to human body and its half-life in blood is quite short. The major harmful substance in tobacco is tar, and the tar in tobacco is composed of thousands of ingredients, tens of which are cancerogenic substances. At present, it has been proven that passive smoking can be harmful to non-smokers.

Some cigarette substitutes that contain only nicotine without tar have been proposed, and many of them, such as "nicotine patch", "nicotine mouthwash", "nicotine chewing gum", "nicotine drink" etc., are made of pure nicotine. Although these cigarette substitutes are free from tar, their major disadvantage is that an effective peak concentration cannot be reached in the blood of a smoker due to slow absorption of nicotine. In addition, these cigarette substitutes cannot satisfy habitual smoking actions of a smoker, for example, inhaling action or sucking action, and thus are not likely to be widely accepted as effective substitutes for quitting smoking.

SUMMARY OF THE INVENTION

An objective of the present invention is to provide an electronic cigarette that overcomes the above-mentioned disadvantages and provides a cigarette that looks like a normal cigarette. The electronic cigarette, which is an integrated assembly resembling a cigarette holder, includes a shell, a cell, nicotine solution, a control circuit, a high temperature vaporization nozzle and accessories. An electrothermal vaporization nozzle is arranged within an air suction end of the shell. The control circuit provides starting current to the electric heater within the vaporization nozzle. Under the high temperature in the vaporization nozzle, the liquid is rapidly vaporized to form a puff of smoke. The cell which provides power to the electric heater via the control circuit can be a disposable battery or a rechargeable battery.

The advantages of the present invention include smoking without tar, significantly reducing the cancerogenic risk. Furthermore, users still feel as if they are smoking, and the cigarette has no need to be lit and has no fire risk.

DETAILED DESCRIPTION OF THE INVENTION

Figure 1:
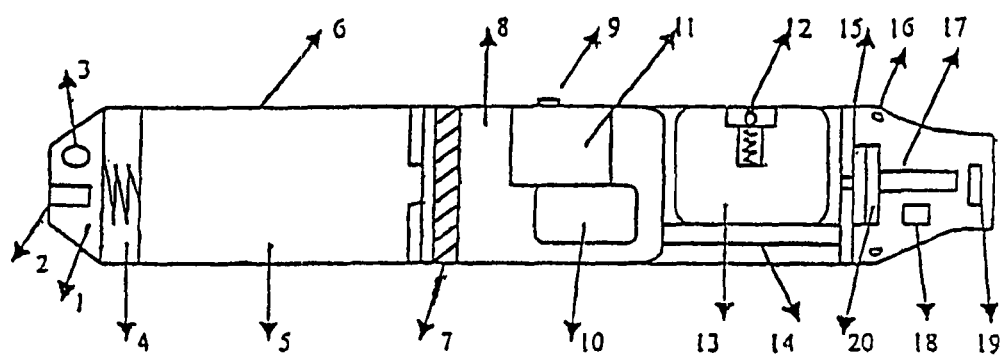
FIG. 1 is a structural diagram of the device in the first example in accordance with the present invention.
Figure 2:
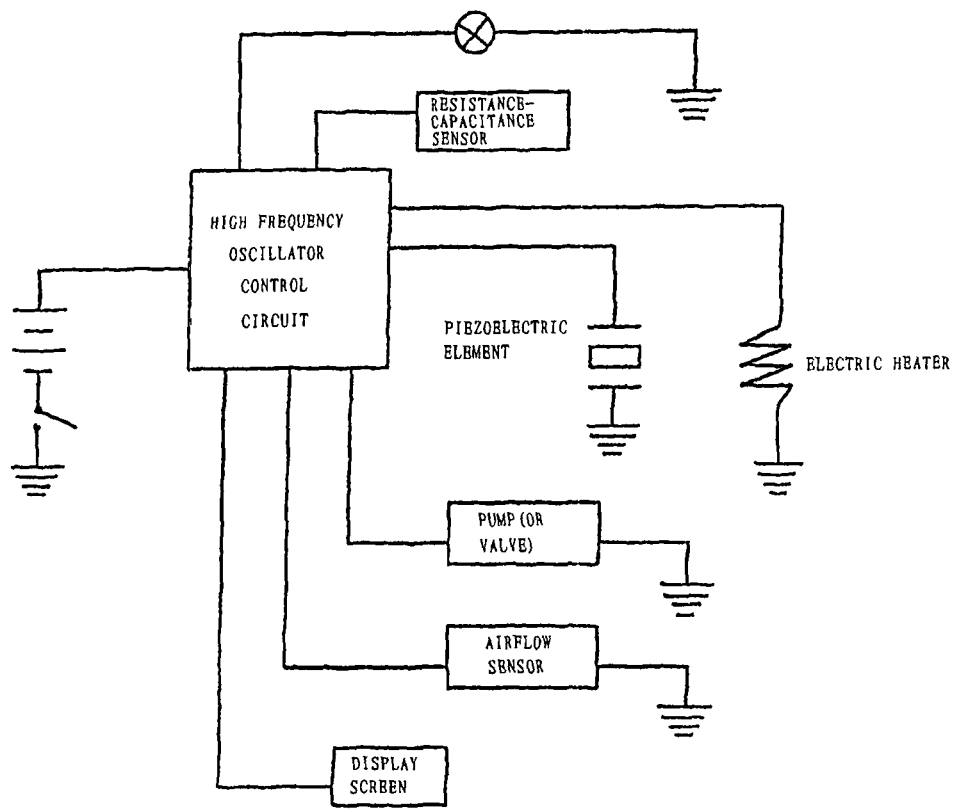
FIG. 2 is a block diagram of the circuit structure.

The high frequency generator of a control circuit board 8 is composed of a capacitance connecting three point type oscillator, an inductance connecting three point type oscillator, or a transformer-type oscillating circuit, which has the frequency of 35 KHz to 3.3 MHz. The circuit includes an automatic frequency fine-adjusting circuit resonating with a piezoelectric element 20. A nicotine solution storage container 13 is made of silicon rubber, alternatively, other polymers that can be protected against the penetration of nicotine can be used. A one-way valve for liquid injection 12 is sealed by a ball or cone member under the pressure of a spring. An airflow sensor 18 can be comprised of an array of integrated thermal sensitive resistors in the shape of film. The electrode of a resistance or capacitance sensor 19, which is sensitive to touches of human body, is composed of an upper metal film and a lower metal film and located at the end of the cigarette holder. The changes of the resistance or capacitance parameters due to human touch are inputted into the control circuit to perform the operation of a body sensitive switch.

The electric controlled pump 11, driven by a motor or a linear motor, drives a retarder that has a large speed ratio, via a shaft coupling, to revolve at a low speed but with large torque. The pump can be a peristaltic pump, a plunger pump, an eccentric pump or a screw pump. Alternatively, the liquid pump can use piezoelectric pump, a super magnetostrictive pump, a thermal expansion drive pump, a thermal contraction drive pump, a thermal bubble pump. The electric control pump or valve may be thermal contractible.

The valve is formed on a silicon rubber tube by nickel-titanium memory alloy or copper-based memory alloy under the force of electro-thermal contractions.

The electro-thermal vaporization nozzle 17 is made of high-temperature resistant materials with low thermal conductivity. The nozzle 17 is a tubule, with the internal diameter of 0.05-2 mm and the effective working length of 3-20 mm. An electric heating element is provided within the nozzle, and the shapes of the electric heating element and the cavity of the nozzle are designed to facilitate vaporization and ejection of liquid. The vaporization nozzle 17 may be made of conventional ceramics, or be made of aluminum silicate ceramics, titanium oxide, zirconium dioxide, yttrium oxide ceramics, molten silicon, silicon dioxide, molten aluminum oxide. The vaporization nozzle 17 may be in the shape of straight tube or spiral, and may also be made from polytetrafluoethylene, carbon fiber, glass fiber or other materials with similar properties.

The electric heating element arranged within the vaporization nozzle 17 may be made of wires of nickel chromium alloy, iron chromium aluminum alloy, stainless steel, gold, platinum, tungsten molybdenum alloy, etc., and may be in the shape of straight line, single spiral, double spiral, cluster or spiral cluster, wherein the straight line and cluster are preferred. The heating function of the electric heating element may be achieved by applying a heating coating on the inner wall of the tube, and the coating may be made from electro-thermal ceramic materials, semiconductor materials, corrosion-resistant metal films, such as gold, nickel, chromium, platinum and molybdenum. The method for coating can include a coat sintering process, a chemical deposition sintering process and an ion spraying process. The materials mentioned above can be provided within the inner wall of vaporization nozzle in any of the processes mentioned above.

Figure 11:
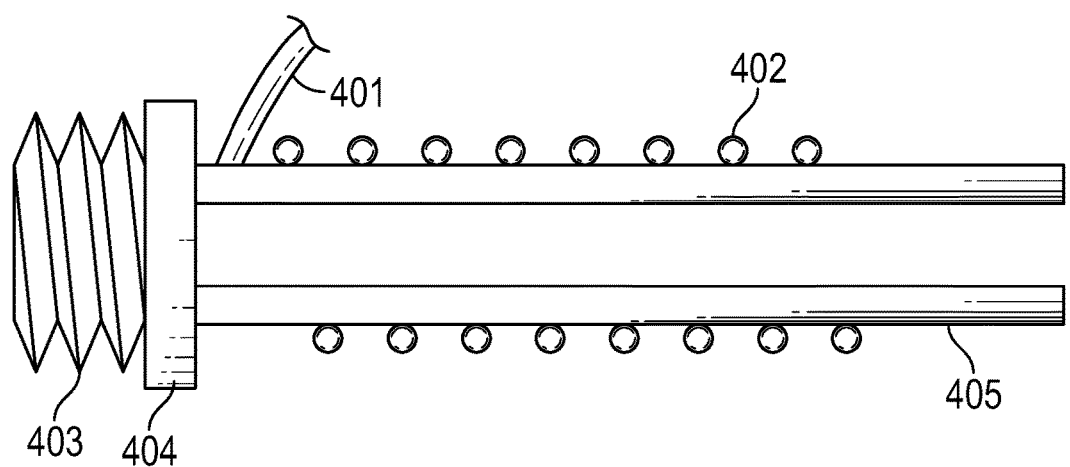
FIG. 11 is a schematic diagram of the structure of an alternative high temperature vaporization nozzle and the electric-thermal element.

The nozzle with high resistance, made of metal, can have no electric heating element being attached, and can be directly applied with heating current. Alternatively, as shown in FIG. 11, the materials mentioned above can be arranged outside of the nozzle in any of the ways mentioned above, and an appropriate response time can also be achieved in the power supply mode of short-term preheating. Nicotine solution used in the atomization process comprises nicotine, propylene glycol, glycerol, organic acids, anti-oxidation agents, essence, water and alcohol, in which the nicotine content is 0.1%-6%, propylene glycol content 80%-90%, organic acids 0.2%-20%, the rest is glycerol, essence, anti-oxidation agents, water and alcohol.

Example 1: The Structural Diagram of the Device Shown in FIG. 1

When a smoker puts the cigarette holder on his/her mouth, the resistance sensor 19 activates the control circuit board 8. The control circuit board 8 then outputs two driving voltages respectively, one used to supply power to the electric heating element of the vaporization nozzle 17 and the other used to activate the micro pump 11 (shown in FIG. 6). The stored solution is then pumped to the nozzle 17 by the solution storage container 13. On the electric heating element of the nozzle 17, the nicotine solution is then vaporized into high temperature vapor which is subsequently ejected from the opening end. In the air, the vapor ejected out is then expanded and condensed into micro aerosol droplets.

The effect of the ultrasonic piezoelectric element 20 mounting on the nozzle is that, firstly, the large liquid droplets in the unstable thermal airflow under high pressure will be in sufficient contact with the electric heating element, and thereby be vaporized. Secondly, the liquid droplets in the nozzle 17 are directly fragmented and atomized. Thirdly, possible bumping when the liquid is above a boiling point will be avoided. The effect of integrated atomization will allow aerosol droplets with diameters of 0.2-3 um to enter into the alveolus easily and be absorbed. The airflow sensor 18 is sensitive to the diluted air which enters through air inlet 16 when a "suction" action take places. The sensed signals are transmitted to the control circuit, and the control circuit then stops supplying power to the micro pump and the electric heater after a certain time delay.

The relay relationship between the time delays of the micro pump and electric heater is as follows: after the electric heater is activated, the micro pump is activated after a time delay of 0.1-0.5 seconds; the electric heater is then turned off after a time delay of 0.2-0.5 seconds when the control circuit of the micro pump is turned off, so as to guarantee a complete vaporization of the liquid after quantitative liquid injection without any leftovers.

Figure 6:
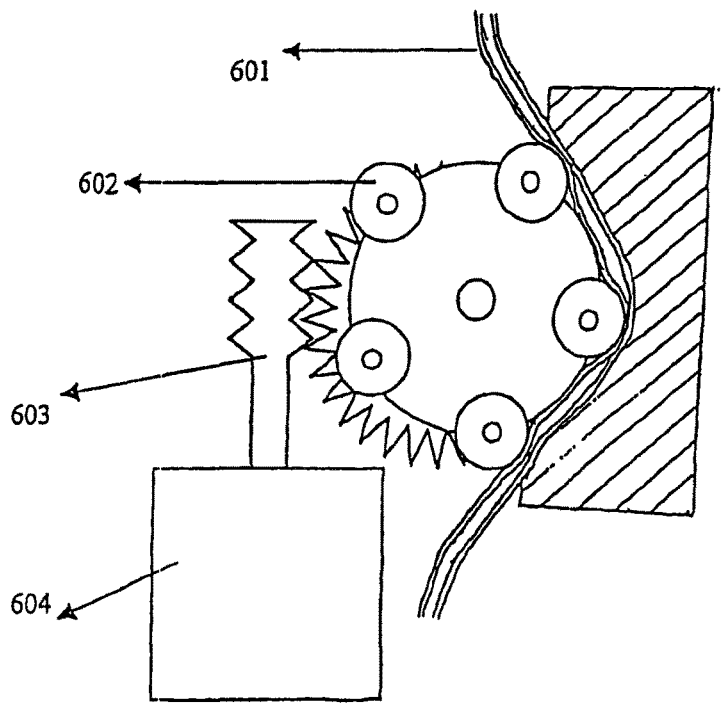
FIG. 6 is a schematic diagram of the peristaltic pump.

The nicotine solution container may be designed to be different sizes as required. The nicotine solution may be refilled once a day, or once a couple of days. The liquid crystal display screen 10 can show operating state parameters, such as cell capacity, smoking times per day, average using cycle and warnings for over smoking. A red LED 3 blinks for each smoking action, and a sawtooth wave signal that lasts for 1.2 seconds is given by the control circuit for blinking signals, which provides a gradual change of luminance to imitate the ignition and combustion process of a conventional cigarette. The charger 1, charging jack 2, spring 4, shell 6, threads 7, switch 9, passage tube 14 and baffle plate 15 are shown in FIG. 1. The silicon gel tube 601, pinch roller 602, worm 603 and motor 604 are shown in FIG. 6.

The control circuit and the ultrasonic micro pump may be integrated on one single chip by using a Micro Electronic Mechanical System (MEMS).

Example 2: The Simplified Electronic Cigarette

Figure 7:
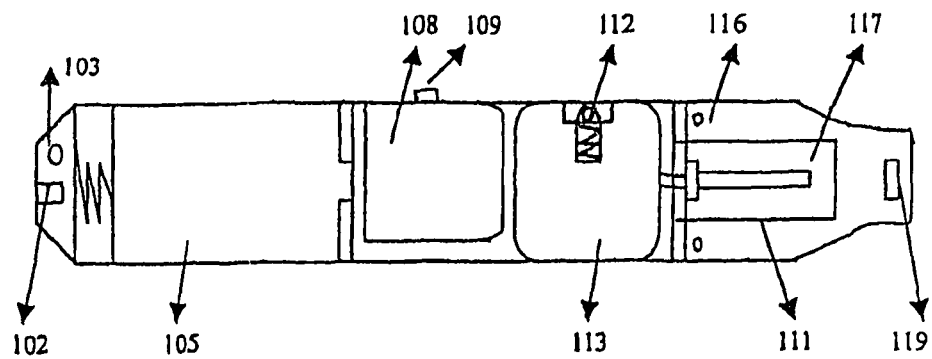
FIG. 7 is a structural diagram of the electronic cigarette in a second example.

FIG. 7 is a structural diagram of the simplified device in which the ultrasonic atomization high frequency generator and the piezoelectric ceramic element 20 are omitted. To achieve a desirable atomization effect, tiny heating wires are used in combination with the nozzle (see FIG. 3), so that the maximum diameters of one or more vaporization cavities formed between the heating wire and the inner wall of the nozzle range from 0.02 mm to 0.6 mm. The function of the airflow sensor 18 omitted is replaced by the manner that the initial signal of the resistance or capacitance sensor 119 is delayed a certain time via the control circuit and acts as the ending signal. The electronic cigarette is configured as follows: the vaporization nozzle 117, the thermal drive pump 111 (see FIG. 5) made of nickel titanium memory alloy wire, and the liquid storage container 113 connected to the thermal drive pump constitute a liquid transmission system. Two outputs of the control circuit board 108 are respectively connected to the electric heater and the pump or valve. A body sensitive resistance sensor 119 is connected to the input of the control circuit. The cell 105 and red LED 103 are provided in the front end within the shell, and resemble a cigarette holder, a pipe or a pen.

The thermal drive pump is an electro-thermal shrinkable peristaltic pump, made of wires of nickel titanium memory alloy or copper based alloy, with gel tube which is pressed at three points respectively during the process of electrothermal contraction to form a pressure cavity for pumping out liquid. The change of volume of the cavity within the thermal drive pump determines the quantity of the solution to be atomized each time. Upon contacting with user's mouth, the resistance sensor 119 activates the control circuit 108, the control circuit 108 then provides operating current to the thermal drive pump and the electric heater, and the output of the control circuit is turned off after the delay of 2 seconds for reactivation at the next smoking action. Alternatively, a thermal expansion drive pump or a thermal bubble pump is also applicable. The thermal expansion drive pump forms a pressure cavity for pumping out liquid by allowing a micro hydrogen container with an embedded electric heating element to block the liquid inlet and open the liquid outlet at the time of thermal expansion. The charging jack 102, LED 103, cell 105, switch 109, liquid-refilling valve 112 and air hole 116 are shown in FIG. 7.

Figure 3:
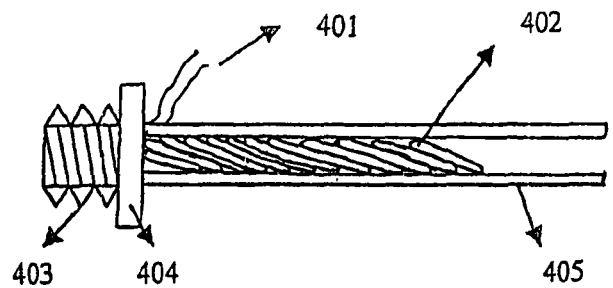
FIG. 3 is a schematic diagram of the structure of the high temperature vaporization nozzle and the electric-thermal element.
Figure 5:
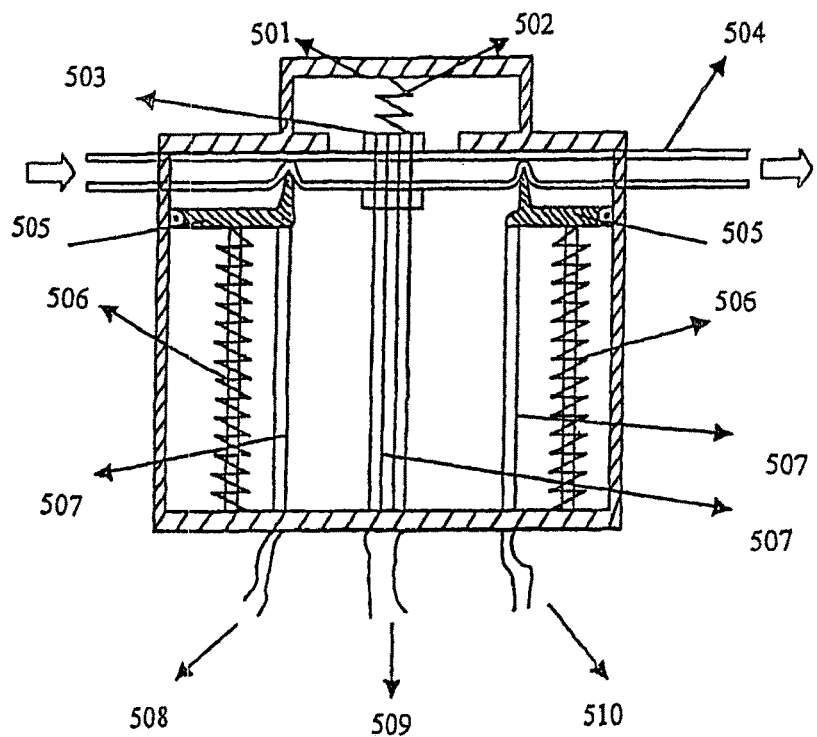
FIG. 5 is a schematic diagram of the peristaltic pump made of memory alloy.

The electrode lead wire 401, heating wire 402, thread 403, base 404 and nozzle 405 are shown in FIG. 3. The support 501, extension spring 502, pumping-out pressure plate 503, silicon gel tube 504, stop pressure plate 505, supporting spring 506, memory alloy wire 507, electrode A 508, electrode B 509 and electrode 510 are shown in FIG. 5.

Example 3: The Electronic Cigarette Made of a Ni—Ti Memory Alloy

Figure 8:
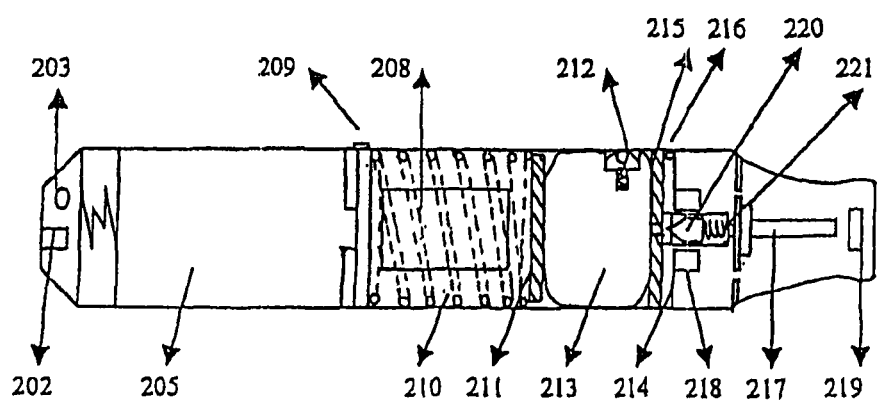
FIG. 8 is a structural diagram of the electronic cigarette in a third example.

FIG. 8 is a structural diagram of the electronic cigarette. The electro-thermal vaporization nozzle 217 of the device is connected to the liquid storage container 213 via a pneumatic valve 220. The super elastic member 210 is connected to the pressure plate 211 which is connected to the liquid storage container 213. The pneumatic valve is composed of a pneumatic film 214, a magnetic steel ring 218, a steel valve needle 220 and a reset spring 221. The super elastic member 210, which is made of Ni—Ti memory alloy, is used to apply a constant pressure on the liquid storage container via the pressure plate 211. When the pneumatic valve opens, the liquid with nicotine enters the vaporization nozzle from the liquid storage container via the pneumatic valve and is vaporized and condensed subsequently to form a puff of smoke at high temperature. Upon contacting with user's mouth, the resistance sensor activates the control circuit to supply power to the electric heater. When the user performs suction action, the Nd—Fe—B permanent magnetic alloy ring attracts the valve needle to move in response to the pneumatic film being subjected to negative pressure. Liquid is supplied when the valve needle opens, and after the pneumatic valve is reset, power supply to the electric heater is turned off after the delay of 0.5 seconds by the control circuit. The LED 203, charging jack 202, cell 205, control circuit 208, switch 209, refilling valve 212, baffle plate 215, air hole 216 and resistance sensor 219 are shown in FIG. 8

Figure 9:
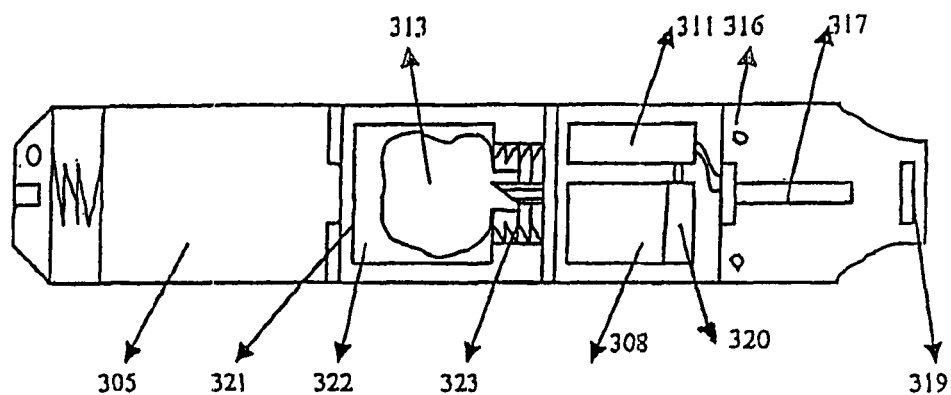
FIG. 9 is a structural diagram of the electronic cigarette in a fourth example.

Example 4: The Electronic Spray Cigarette Utilizing the Pressure of a Container In the device (see FIG. 9), the electro-thermal vaporization nozzle 317, the electronic valve 311 connected with the metering cavity 320, and the liquid storage container 313 form a liquid transmission passage. A gas vessel filled with high-pressure nitrogen is arranged around the periphery of the liquid storage container to exert pressure thereon to facilitate the transmission of the liquid. When a control signal is applied to the electronic valve, the electronic valve is activated, and the solution with nicotine enters the metering cavity from the liquid storage container under pressure. The solution pushes a piston so as to allow a constant volume of liquid at the other side of the piston to enter the vaporization nozzle via the electronic valve. The metering cavity provided at the valve is a cylinder having a liquid inlet and a liquid outlet. Located within the cylinder are the piston micro holes and the reset spring connected onto the piston. The control circuit which is activated by the resistance sensor 319 controls the states of the electronic valve and the electric heater respectively. Due to slow infiltration of the micro hole of the piston in the metering cavity and the force of the reset spring, the piston returns to its original position within 5-8 seconds after each atomization process. The cell 305, pressure vessel 321, pressure chamber 322, seal threaded-opening 323, control circuit board 308 and air hole 316 are showed in FIG. 9.

Figure 4:
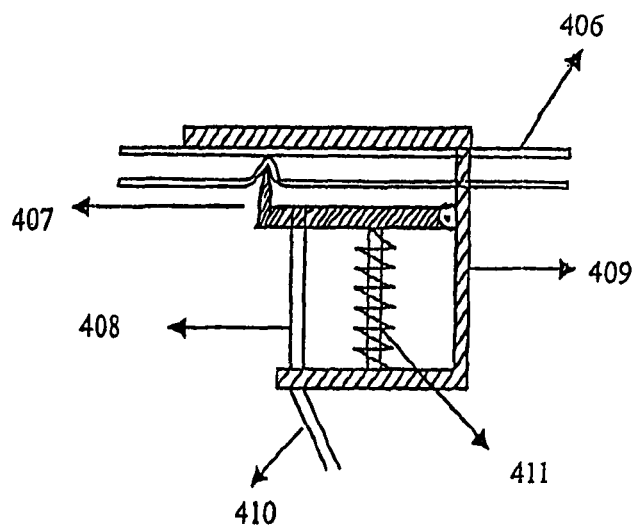
FIG. 4 is a schematic diagram of the valve made of memory alloy.
Figure 10:
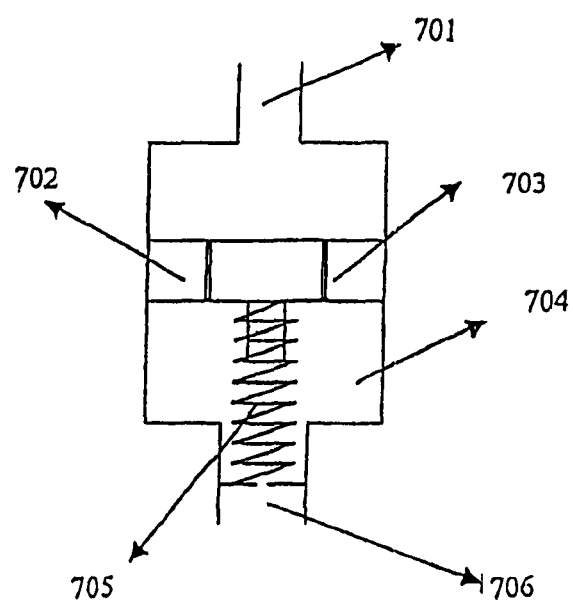
FIG. 10 is a structural diagram of the metering cavity in the fourth example.

The silicon gel tube 406, pressure-stopping plate 407, memory alloy wires 408, support 409, electrode lead wire 410 and pressure spring 411 are shown in FIG. 4. The inlet 701, piston 702, micro hole of the piston 703, metering cavity 704, reset spring 705 and outlet 706 are shown in FIG. 10.

The recipes of nicotine solution used are:
 1. 6% nicotine, 85% propylene glycol, 2% glycerol, 2% essence, 1% organic acid and 1% anti-oxidation agent;
 2. 4% nicotine, 80% propylene glycol, 5% glycerol, 1% butyl valerate, 1% isopentyl hexonate, 0.6% lauryl laurate, 0.4% benzyl benzoate, 0.5% methyl octynicate, 0.2% ethyl heptylate, 0.3% hexyl hexanoate, 2% geranyl butyrate, 0.5% menthol, 0.5% citric acid and 4% tobacco essence;
 3. 2% nicotine, 90% propylene glycol, 2.5% citric acid, 1% essence and 4.5% tobacco essence;
 4. 0.1% nicotine, 80% propylene glycol, 5% glycerol, 8% alcohol, 2.9% water, 1% essence, 1% tobacco essence and 2% organic acid.

I claim:
1. A vaporizing device, comprising:
 a rechargeable battery in a housing, the rechargeable battery electrically connected to a control circuit;
 a charging connector in the housing for charging the rechargeable battery;
 an LED in the housing electrically connected to the control circuit;
 at least one air inlet for allowing air to flow into the housing;
 a wire coil heating element inside of the housing, the wire coil heating element electrically connected to the control circuit, and with the wire coil heating element having a length aligned along and in contact with a length of fiber material;
 a liquid storage container holding a liquid movable into contact with the fiber material;
 the at least one air inlet leading into an air flow path in the housing to an outlet on the housing, with the length of fiber material in the air flow path; and
 the wire coil heating element vaporizing liquid from the liquid storage container.
2. The vaporizing device of claim 1 further including an air flow sensor positioned to sense air flow in the air flow path, with the air flow sensor electrically connected to the control circuit.

3. The vaporizing device of claim 1 further including a switch electrically connected to the control circuit for switching on the wire coil heating element.

4. The vaporizing device of claim 1 with the charging connector at a first end of the housing.

5. The vaporizing device of claim 1 wherein the wire coil heating element is wrapped around the length of fiber material.

6. The vaporizing device of claim 1 wherein the fiber material comprises glass fiber.

7. The vaporizing device of claim 1 further comprising a passageway providing liquid to the length of the fiber material.

8. The vaporizing device of claim 1 wherein the length of fiber material is longer than the wire coil heating element.

9. The vaporizing device of claim 1 with the length of fiber material in between the rechargeable battery and an outlet on a mouthpiece.

10. The vaporizing device of claim 1 wherein the length of fiber material has a free end.

11. The vaporizing device of claim 1 with the length of fiber material supported on a base and further including an electrode lead adjacent to the base and electrically connected to the wire coil heating element.

12. The electronic vaporizing device of claim 2 with the control circuit configured such that luminance of the LED changes based on an output of the air flow sensor.

13. The electronic vaporizing device of claim 2 with the control circuit configured to control luminance of the LED when the air flow sensor senses airflow, such that the LED simulates the appearance of a conventional burning cigarette tip.

14. The electronic vaporizing device of claim 1 with the housing having a first section attached to a second section, and with the rechargeable battery in the first section.

15. A vaporizing device, comprising:
a first housing attachable to and detachable from a second housing;
a rechargeable battery in the first housing electrically connected to a control circuit;
a charging connector in the first housing electrically connected to the rechargeable battery;
the first housing having an LED electrically connected to the control circuit;
at least one air inlet for allowing air to flow into the second housing;
a heating element comprising a wire coil inside of the second housing, the heating element electrically connected to the control circuit, and with the heating element contacting a fiber material;
the second housing containing a liquid movable into contact with the fiber material;
the at least one air inlet connecting into an air flow path in the second housing leading to an outlet on the second housing; and
the heating element vaporizing the liquid.

16. The vaporizing device of claim 15 further including an air flow sensor electrically connected to the control circuit.

17. The vaporizing device of claim 15 further including a switch electrically connected to the control circuit for switching on the wire coil.

18. The vaporizing device of claim 15 with the liquid in a liquid container in the second housing.

19. The vaporizing device of claim 15 wherein the wire coil is wrapped around the fiber material.

20. The vaporizing device of claim 19 wherein the fiber material comprises glass fiber.

21. The vaporizing device of claim 15 further comprising a passageway providing liquid to the fiber material.

22. The vaporizing device of claim 15 with the fiber material in between the rechargeable battery and an outlet on a mouthpiece.

23. The vaporizing device of claim 15 with the fiber material having a free end.

24. The vaporizing device of claim 15 with the fiber material supported on a base and further including an electrode lead adjacent to the base and electrically connected to the wire coil.

25. A vaporizing device, comprising:
a first housing attachable to and detachable from a second housing;
a rechargeable battery in the first housing electrically connected to a control circuit;
a charging connector in the first housing electrically connected to the rechargeable battery;
the first housing having an LED electrically connected to the control circuit;
at least one air inlet for allowing air to flow into the second housing;
a wire coil inside of the second housing, the wire coil electrically connected to the control circuit, and the wire coil wound around and contacting a fiber material, the fiber material longer than the wire coil;
the second housing containing a liquid movable into contact with the fiber material;
the at least one air inlet connecting into an air flow path in the second housing leading to an outlet in a mouthpiece on the second housing;
the fiber material in between the rechargeable battery and the outlet;
an air flow sensor positioned to sense air flow in the air flow path, with the air flow sensor electrically connected to the control circuit; and
the wire coil vaporizing the liquid.

26. The vaporizing device of claim 25 with the fiber material having a free end.

27. The vaporizing device of claim 25 with the fiber material supported on a base and further including an electrode lead adjacent to the base and electrically connected to the wire coil.

* * * * *